(12) United States Patent
Komsa et al.

(10) Patent No.: US 11,723,634 B2
(45) Date of Patent: Aug. 15, 2023

(54) ADAPTER ASSEMBLY FOR ATTACHING A LIGHTING DEVICE TO A HANDHELD ELECTROSURGICAL INSTRUMENT

(71) Applicant: Pathy Medical, LLC, Shelton, CT (US)

(72) Inventors: James Komsa, Shelton, CT (US); Vinod V. Pathy, Madison, CT (US); Gennady Kleyman, Brooklyn, NY (US); Mikiya Silver, New Haven, CT (US)

(73) Assignee: Pathy Medical, LLC, Shelton, CT (US)

( * ) Notice: Subject to any disclaimer, the term of this patent is extended or adjusted under 35 U.S.C. 154(b) by 0 days.

(21) Appl. No.: 17/878,481

(22) Filed: Aug. 1, 2022

(65) Prior Publication Data

US 2022/0361860 A1 Nov. 17, 2022

Related U.S. Application Data

(63) Continuation of application No. 16/653,085, filed on Oct. 15, 2019, now Pat. No. 11,426,150.
(Continued)

(51) Int. Cl.
*A61B 17/00* (2006.01)
*A61B 90/30* (2016.01)
*F21Y 115/10* (2016.01)

(52) U.S. Cl.
CPC .............. *A61B 17/00* (2013.01); *A61B 90/30* (2016.02); *A61B 2017/00017* (2013.01);
(Continued)

(58) Field of Classification Search
CPC .................. A61B 17/00; A61B 90/30; A61B 2017/00017; A61B 2017/00486;
(Continued)

(56) References Cited

U.S. PATENT DOCUMENTS

| | | | |
|---|---|---|---|
| 6,428,180 B1 * | 8/2002 | Karram | ............... A61B 5/0059 362/120 |
| 6,988,814 B1 | 1/2006 | Correa | |

(Continued)

FOREIGN PATENT DOCUMENTS

| | | |
|---|---|---|
| EP | 2027824 A1 | 2/2009 |
| JP | 2017094126 A | 6/2017 |

(Continued)

OTHER PUBLICATIONS

PCT International Search Report and Written Opinion dated Feb. 6, 2020, issued during the prosecution of PCT International Patent Application No. PCT/US2019/056356.
(Continued)

*Primary Examiner* — Tsion Tumebo
(74) *Attorney, Agent, or Firm* — Locke Lord LLP; Scott D. Wofsy; Michael J. Pollack

(57) ABSTRACT

An adapter assembly is disclosed for attaching a lighting device to a handheld surgical instrument, which includes a first body portion configured to engage a distal end portion of the surgical instrument at a position along a central axis thereof, and a second body portion configured to support a lighting device adjacent the distal end portion of the surgical instrument, such that an illumination axis of the lighting device angularly intersects the central axis of the surgical instrument.

8 Claims, 22 Drawing Sheets

Related U.S. Application Data

(60) Provisional application No. 62/746,927, filed on Oct. 17, 2018.

(52) U.S. Cl.
CPC ............... *A61B 2017/00486* (2013.01); *A61B 2017/00734* (2013.01); *F21Y 2115/10* (2016.08)

(58) Field of Classification Search
CPC .. A61B 2017/00734; A61B 2018/1412; A61B 18/1402; A61B 90/35; A61B 2017/00477; A61B 2017/00738; A61B 2090/309; A61B 18/148; A61B 50/20; A61B 2018/00172; A61B 2018/0091; A61B 2560/0204; A61B 2560/0431; F21Y 2115/10

See application file for complete search history.

(56) References Cited

U.S. PATENT DOCUMENTS

| | | |
|---|---|---|
| 9,851,060 B2 | 12/2017 | Pathy |
| 2002/0058931 A1 | 5/2002 | Parker et al. |
| 2006/0271096 A1 | 11/2006 | Hamada |
| 2010/0091483 A1 | 4/2010 | Henry et al. |
| 2011/0176309 A1 | 7/2011 | Lin |
| 2012/0078279 A1* | 3/2012 | Mark ................. A61B 10/0275 606/171 |
| 2012/0101497 A1 | 4/2012 | Jayaraj |
| 2013/0197317 A1 | 8/2013 | Daniel et al. |
| 2013/0331657 A1 | 12/2013 | Basson et al. |
| 2014/0293590 A1 | 10/2014 | Pathy |
| 2018/0153635 A1* | 6/2018 | Preissman .......... A61B 18/1402 |
| 2018/0318034 A1 | 11/2018 | Ibanez et al. |

FOREIGN PATENT DOCUMENTS

| | | |
|---|---|---|
| KR | 2016-0000939 A | 1/2016 |
| WO | 2017-001379 | 1/2017 |

OTHER PUBLICATIONS

PCT International Search Report and Written Opinion dated Oct. 15, 2019, issued during the prosecution of PCT International Patent Application No. PCT/US2019/056356.

Extended European Search Report dated Nov. 10, 2022, issued during the prosecution of European Patent Application No. 19874652.1.

* cited by examiner

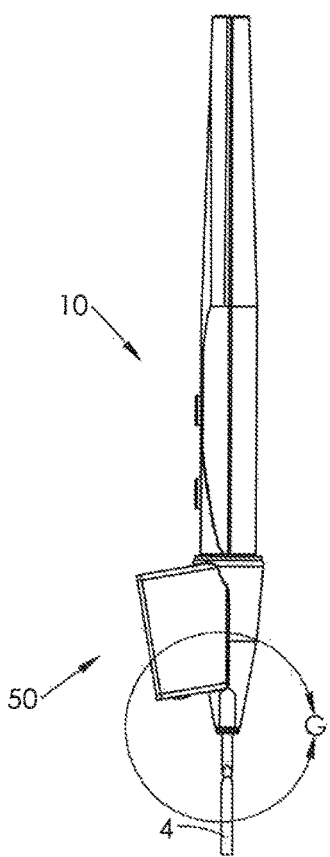
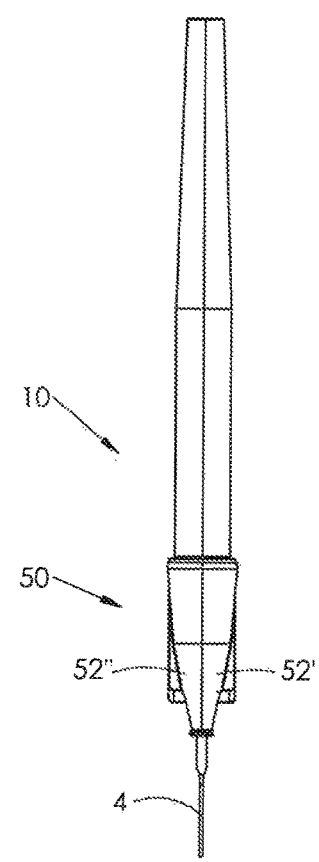
FIG. 21    FIG. 22    FIG. 23
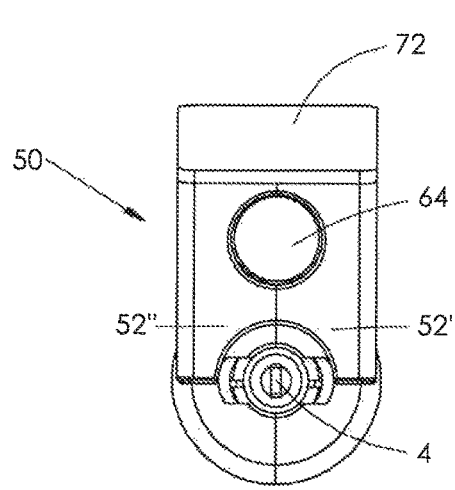
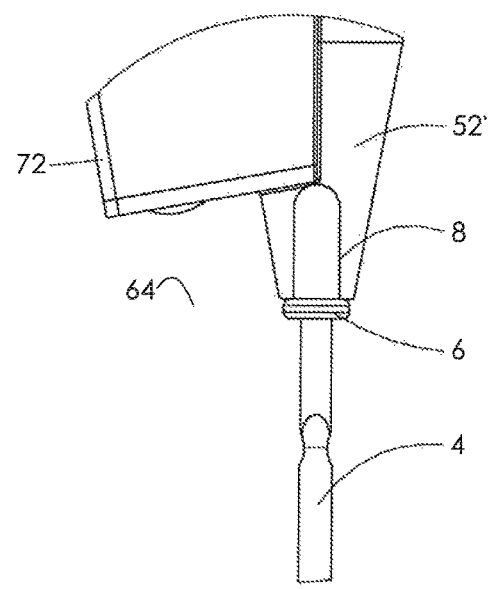
FIG. 24    FIG. 25

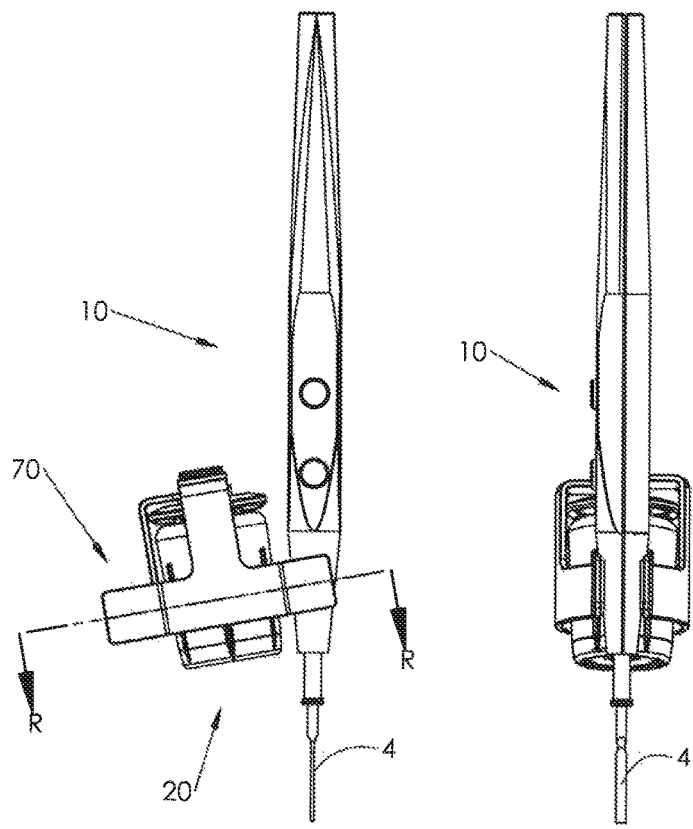
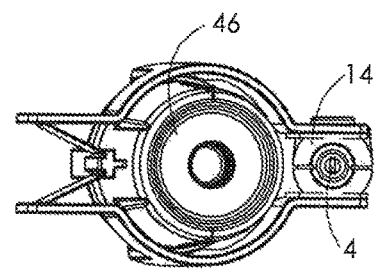
FIG. 57  FIG. 58  FIG. 59
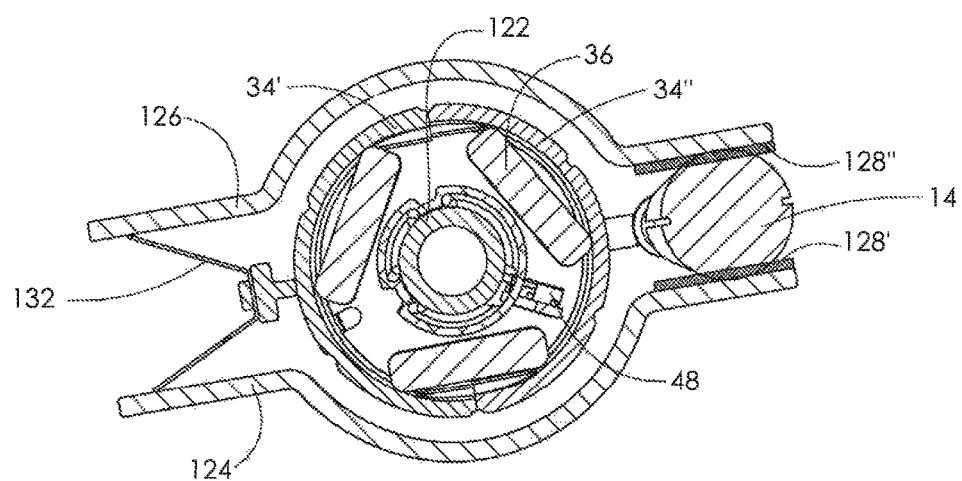
FIG. 60

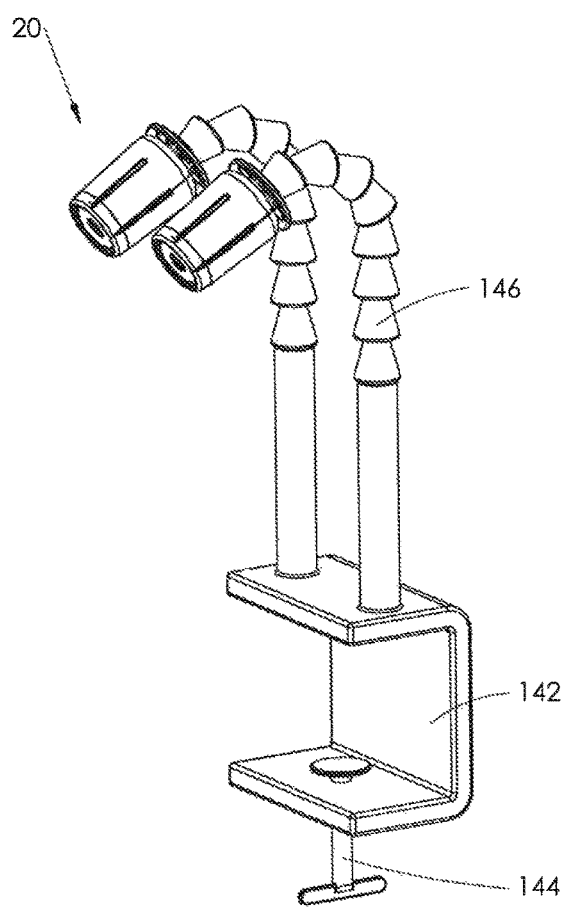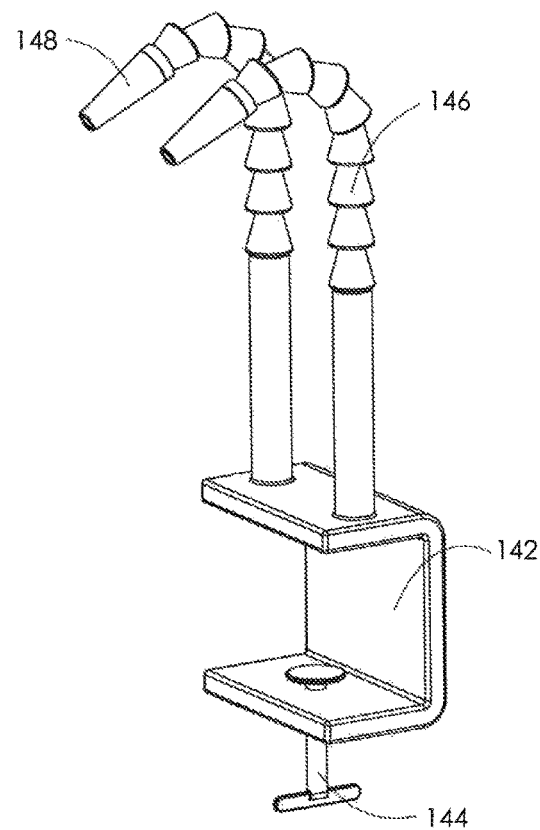
FIG. 77
FIG. 78

ADAPTER ASSEMBLY FOR ATTACHING A LIGHTING DEVICE TO A HANDHELD ELECTROSURGICAL INSTRUMENT

CROSS REFERENCE TO RELATED APPLICATIONS

This Application is a Continuation of U.S. patent application Ser. No. 16/653,085 filed on Oct. 15, 2019, which claims the benefit of priority to U.S. Provisional Patent Application No. 62/746,927, filed on Oct. 17, 2018. The entire contents of these applications is incorporated herein by reference in their entireties.

BACKGROUND OF THE INVENTION

1. Field of the Invention

The subject invention is directed to surgical instrumentation, and more particularly, to an adapter assembly for attaching a battery powered lighting device to a handheld electrosurgical instrument.

2. Description of Related Art

Lighting devices are typically used to allow an operator to illuminate, and thus more precisely control and enhance, a space or area with a lighted field of view. In many situations, a lighting device can be used to illuminate a closed or confined space that would not regularly receive an adequate amount of light, if at all.

Existing lighting devices are connectable to a variety of tools, including, for example, medical devices and hand tools such as screwdrivers, to illuminate the area in which the device or tool is to be used. Such lighting devices and light sources include attachments that have an electrical cord extending therefrom that in turn is connectable to a power source, attachments that are battery powered, and light sources integrally formed within a tool to direct light on a specific field of view.

In medical practice, lighting devices are used to direct light at a specific area being operated on or examined. For example, lighting devices can be used in conjunction with handheld electrosurgical devices, such as an electrosurgical pencils or more specifically a BOVIE® pencil used to incise through tissues, and a variety of other operative instruments, such as retractors and forceps. Lighted retractors are commonly used during surgeries to help illuminate surgical cavities or other areas within the surgical field.

The inventors have discerned a number of disadvantages of previously known lighting devices. For example, known lighting devices that include a light source integrally formed therein are generally expensive, bulky, and can cause injury. Known cordless and corded lighting devices add significant bulk to a tool preventing a user from manipulating the tool with the precision required in many situations and preventing the user from extending the tool into tight spaces.

Additionally, many lighting devices, especially corded lighting devices, require constant repositioning, are cumbersome, are assistant-dependent to hold or re-position, and can be disruptive to a surgical field. Further, corded lighting devices as well as light sources integrally formed within a tool can become hot, burn the user and/or the patient, and possibly even cause a fire.

Headlights can be used as an alternative to a lighting device during a surgical procedure. However, similar to other lighting devices, headlights are bulky, commonly require cables to connect to a power source, require constant readjustment, and can pose a potential safety hazard. In addition, headlamps are not sterile. Moreover, being worn on the head of the surgeon, they are at a distance from the surgical field, decreasing their effectiveness, and can be cumbersome to the user, and cause fatigue if worn for an extended period of time.

A particularly useful lighting device designed for attachment to a handheld electrosurgical device, and in particular, for use with an electrosurgical pencil, is disclosed in U.S. Pat. No. 9,851,060, the disclosure of which is herein incorporated by reference in its entirety. The subject invention provides an accessory for enhancing the utility and effectiveness of the lighting device disclosed therein.

SUMMARY OF THE DISCLOSURE

The subject invention is directed to a new and useful adapter assembly for attaching a battery powered lighting device to a handheld electrosurgical surgical instrument. In general, the adapter assembly of the subject invention includes a first body portion configured to engage a distal end portion of the surgical instrument at a position along a central axis thereof, and a second body portion configured to support a lighting device adjacent the distal end portion of the surgical instrument, such that an illumination axis of the lighting device angularly intersects the central axis of the surgical instrument.

A first embodiment of the adapter assembly of the subject invention includes: a conical sleeve having an interior bore configured to engage a distal end portion of the surgical instrument at a location along a central axis thereof; and a conical shaft connected to the conical sleeve by a flange and configured to engage a central bore of the lighting device, wherein the lighting device includes a plurality of circumferentially arranged light sources and an annular lens located at a distal end thereof to define the illumination axis of the lighting device, and wherein the illumination axis of the lighting device angularly intersects the central axis of the surgical instrument.

The light sources may be comprised of light-emitting diodes, such as blue LEDs, white LEDs, yellow LEDs, etc. LEDs are advantageous because they consume less energy, have a longer lifetime, are available in smaller sizes, and provide faster switching than other types of lights. Nevertheless, other types of lights may also be used. For example, the light sources could be adapted and configured to produce UV light, including UV-C light to treat or prophylax against infectious organisms.

The conical sleeve is bifurcated so as to form flexible conical sections for engaging the distal end portion of the surgical instrument, and it is adapted for axial rotation about the central axis of the surgical instrument. A resilient O-ring is positioned within the interior bore of the conical sleeve for sealing against the distal end portion of the surgical instrument to prevent unwanted axial rotation of the conical sleeve without the application of a rotational force. In addition, an annular jamming ring surrounds the central bore of the lighting device for frictionally engaging the conical shaft, and a switching mechanism is operatively associated with the central bore of the lighting device for activating the LED light sources upon engagement of the conical shaft within the central bore of the lighting device.

A second embodiment of the adapter assembly of the subject invention includes: a conical sleeve having an interior bore configured to engage a distal end portion of the surgical instrument at a position along a central axis thereof;

and a housing formed integral with and extending radially outwardly from the conical sleeve and having an interior chamber for supporting the lighting device, which includes an LED or other light source and an annular lens located at a distal end of the housing to define the illumination axis of the lighting device, wherein the illumination axis of the lighting device angularly intersects the central axis of the surgical instrument.

The conical sleeve is bifurcated so as to form flexible conical sections for engaging the distal end portion of the surgical instrument. This flexible structure will enable the conical sleeve to accommodate or otherwise engage with surgical instruments of different shape, increasing the compatibility of the adapter with different electrosurgical pencils.

The conical sleeve is adapted for axial rotation about the central axis of the surgical instrument. A resilient O-ring is positioned within the interior bore of the conical sleeve for sealing against the distal end portion of the surgical instrument to prevent unwanted axial rotation of the conical sleeve without the application of a rotational force. A switching mechanism is disposed within the housing and it communicates with the conical sleeve for activating the LED or other light source upon engagement of the distal end portion of the surgical instrument with the conical sleeve.

A third embodiment of the adapter assembly of the subject invention includes: a housing having an interior chamber for supporting the lighting device, which includes an LED or other light source and a circular lens located at a distal end of the housing to define the illumination axis of the lighting device; and a clamping mechanism depending from the housing and including a pair of spaced apart engagement flanges adapted for linear movement between an open position for receiving the distal end portion of the surgical instrument and a closed position for engaging the distal end portion of the surgical instrument at a position along a central axis thereof, such that the illumination axis of the lighting device angularly intersects the central axis of the surgical instrument Each engagement flange of the clamping mechanism is provided with an elastomeric plate on interior surface thereof for engaging the distal end portion of the surgical instrument, and the spaced apart engagement flanges are spring biased into the closed position. A switching mechanism is disposed within the housing for activating the LED or other light source upon engagement of the distal end portion of the surgical instrument with the clamping mechanism.

A fourth embodiment of the adapter assembly of the subject invention includes: a conical shaft configured to engage a central bore of the lighting device, wherein the lighting device includes a plurality of circumferentially arranged LED or other light sources and an annular lens located at a distal end thereof to define the illumination axis of the lighting device; and a clamping mechanism including a pair of spaced apart engagement flanges operatively associated with the conical shaft and adapted for pivotal movement between an open position for receiving the distal end portion of the surgical instrument and a closed position for engaging the distal end portion of the surgical instrument along the central axis thereof, such that the illumination axis of the lighting device angularly intersects the central axis of the surgical instrument Each engagement flange of the clamping mechanism is provided with an elastomeric plate on interior surface thereof for engaging the distal end portion of the surgical instrument, and the spaced apart engagement flanges are spring biased into the closed position. An annular jamming ring surrounds the central bore for frictionally engaging the conical shaft. A switching mechanism is operatively associated with the central bore of the lighting device for activating the LED or other light sources upon engagement of the conical shaft within the central bore of the lighting device.

In essence, while the battery powered lighting device disclosed herein is adapted and configured to be installed on the distal end portion of a particular type of electrosurgical pencil, that is relative common in the marketplace, the adapter assemblies disclosed herein enable such a lighting device to be used with a variety of different electrosurgical pencils and even a variety of different types of surgical and non-surgical devices.

Furthermore, it is envisioned that the adapter assemblies disclosed herein could be used to attach the battery powered lighting device disclosed herein to objects, instruments and or equipment other than handheld surgical devices. For example, it is envisioned that adapter assemblies disclosed herein, especially those with a clamping mechanism, could be attached or otherwise clamped to an operating table or to a surgical drape, or even directly clamped to body tissue, so as to support the lighting device in any useful location.

Those skilled in the art will readily appreciate that the adapter assemblies of the subject invention could also be used to attach a lighting device to other types of surgical instruments and devices such as, for example, retractors, snares, hooks, scalpels or staplers. It is also envisioned that specific adaptors can be designed for certain applications or surgeries. For example, an adapter could be designed for a special tool used during a robotic surgical procedure a robotic procedure that uses a very specific tool.

The subject invention is also directed to a kit that includes a handheld surgical instrument, a battery powered lighting device, an adapter for attaching lighting device to the surgical instrument, and a packaging enclosure containing the surgical instrument, the lighting device and the adapter. Preferably, the handheld surgical instrument is an electrosurgical pencil. The adapter contained in the packing enclosure could be any of the adapters disclosed herein.

The subject invention is also directed to an adapter assembly for attaching one or more battery powered lighting devices to a table in a surgical arena. The adapter assembly includes a mounting clamp for releasably attaching the assembly to a table, and a pair of independently adjustable flexible adapter arms each having a conical shaft portion for releasably retaining a respective lighting device.

These and other features of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the subject invention without undue experimentation, preferred embodiments thereof will be described in detail herein below with reference to the figures wherein:

FIG. 21 is a top plan view of the adapter assembly of FIG. 18 mounted on the distal end portion of the handheld electrosurgical instrument;

FIG. 22 is a side elevational view of the adapter assembly of FIG. 18 mounted on the distal end portion of the handheld electrosurgical instrument;

FIG. 23 is a bottom plan view of the adapter assembly of FIG. 18 mounted on the distal end portion of the handheld electrosurgical instrument;

FIG. 24 is a front end view of the adapter assembly of FIG. 18 mounted on the distal end portion of the handheld electrosurgical instrument;

FIG. 25 is an enlarged localized view taken from FIG. 22;

FIG. 57 is a side elevational view of the adapter assembly of FIG. 54 engaged on the distal end portion of the handheld electrosurgical instrument;

FIG. 58 is a bottom plan view of the adapter assembly of FIG. 54 attached on the distal end portion of the handheld electrosurgical instrument;

FIG. 59 is a front end view of the adapter assembly of FIG. 54 attached on the distal end portion of the handheld electrosurgical instrument;

FIG. 60 is a cross-sectional view taken along line R-R of FIG. 57;

FIGS. 73-78 are perspective views of an adapter assembly for attaching one or more battery powered lighting devices to a table or surface, which includes an adjustable support clamp and a pair of independently adjustable flexible adapter arms, each for releasably retaining a lighting device.

DETAILED DESCRIPTION OF THE PREFERRED EMBODIMENTS

Figure 1:
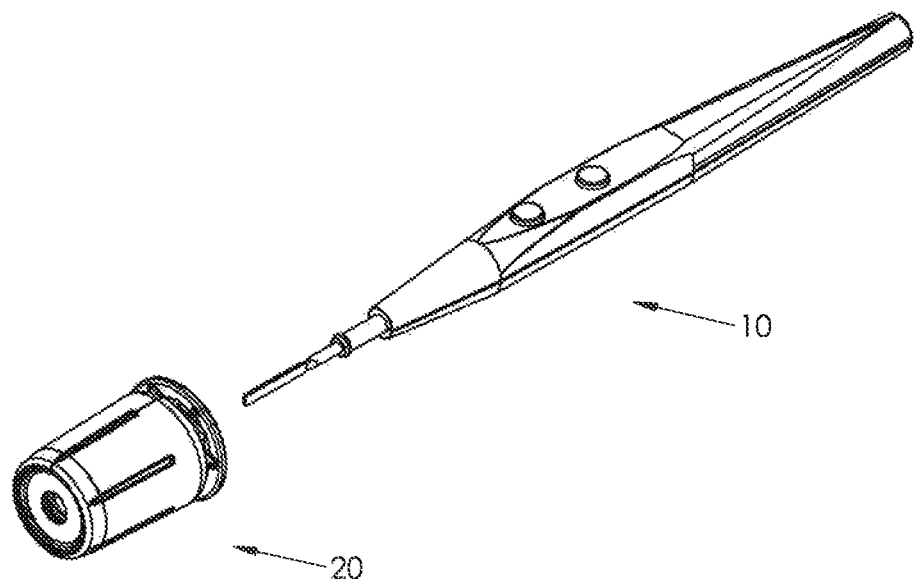
FIG. 1 is a perspective view of a lighting device detached from a handheld electrosurgical instrument.
Figure 2:
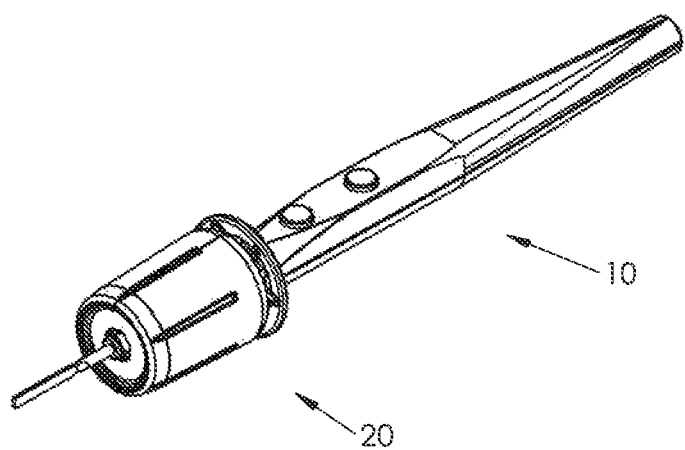
FIG. 2 is a perspective view of the lighting device of FIG. 1 attached on the distal end portion of the handheld electrosurgical instrument.
Figure 3:
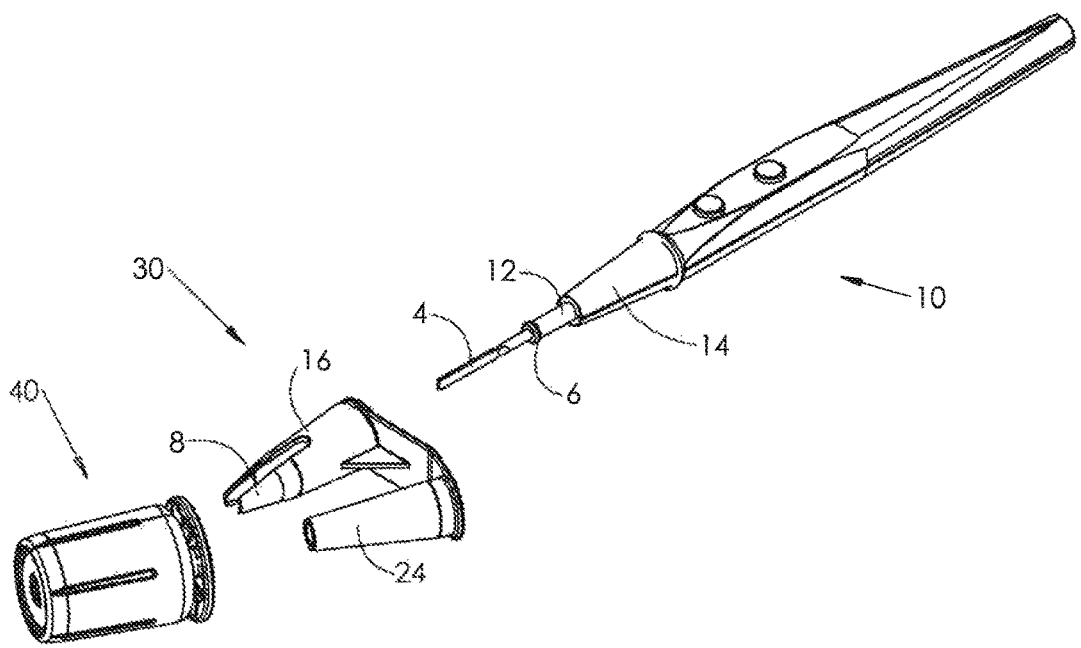
FIG. 3 is an exploded perspective view of a first embodiment of the adapter assembly of the subject invention, separated from the lighting device and the handheld electrosurgical instrument.
Figure 4:
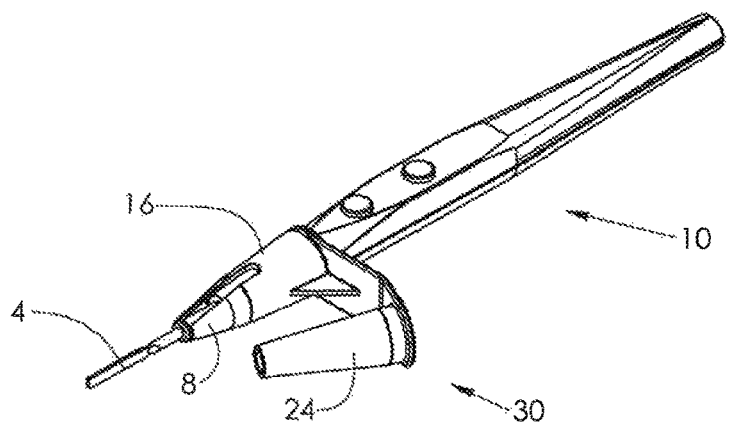
FIG. 4 is perspective view of the first body portion of the adapter assembly of the subject invention engaged on the distal end portion of the handheld electrosurgical instrument.

Referring now to the drawings wherein like reference numerals identify similar structural elements of the various embodiments of the subject invention, there is illustrated in FIGS. 1 and 2, a battery powered cordless lighting device 20 configured for direct installation on the distal end portion of a handheld electrosurgical instrument 10, and more particularly, for direct installation on the distal end portion of an electrosurgical pencil such as a BOVIE pencil, as disclosed, for example, in U.S. Pat. No. 9,851,060. In use, once the lighting device 20 is directly installed on the distal end portion of the electrosurgical instrument 10, an annulus of light automatically and simultaneously projects from the lighting device 20 along the longitudinal axis of the instrument 10.

In contrast to the lighting device 20 illustrated in FIGS. 1 and 2, which is directly installed on the distal end portion of the surgical instrument 10, the subject invention is directed to an adapter assembly for attaching a lighting device, such as the lighting device 20, to the surgical instrument 10 at a location that is adjacent to the distal end portion of the surgical instrument 10.

Referring to FIGS. 3-19, there is illustrated an adapter assembly 30 for attaching a lighting device 40 to a handheld surgical instrument 10 at a location that is adjacent to a distal end portion 14 of the surgical instrument 10. As shown in FIGS. 3-9 and 14, the adapter assembly 30 includes a conical sleeve portion 16 having an interior bore configured to engage the distal end portion 14 of the surgical instrument 10 at a location along a central axis thereof, and a conical shaft portion 24 configured to engage a central bore of the lighting device 40.

As best seen in FIGS. 6-9, 12 and 14, a rigid flange connects the conical sleeve portion 16 of the adapter assembly 30 to the conical shaft portion 24 of the adapter assembly 30. The rigid flange of the adapter assembly 30 is configured in such a manner so that a illumination axis of the lighting device 40 is oriented to angularly intersect a central axis of the surgical instrument 10.

Figure 11:
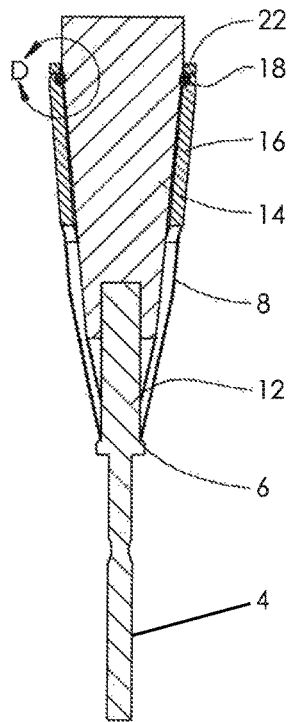
FIG. 11 is a cross-sectional view taken along line B-B of FIG. 7.
Figure 12:
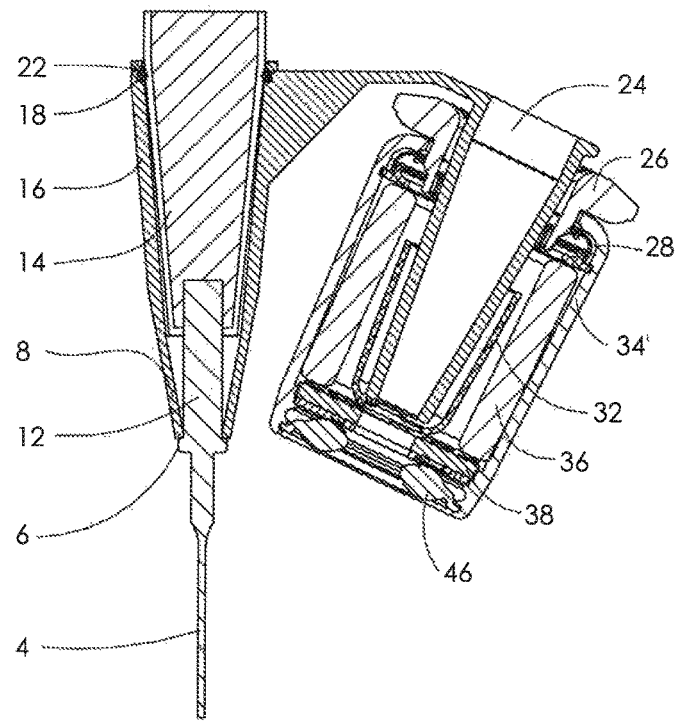
FIG. 12 is a cross-sectional view taken along line C-C of FIG. 8.
Figure 13:
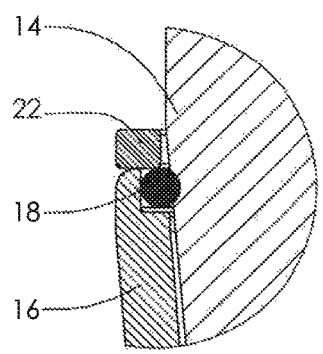
FIG. 13 is an enlarged localized view taken from FIG. 11.
Figure 14:
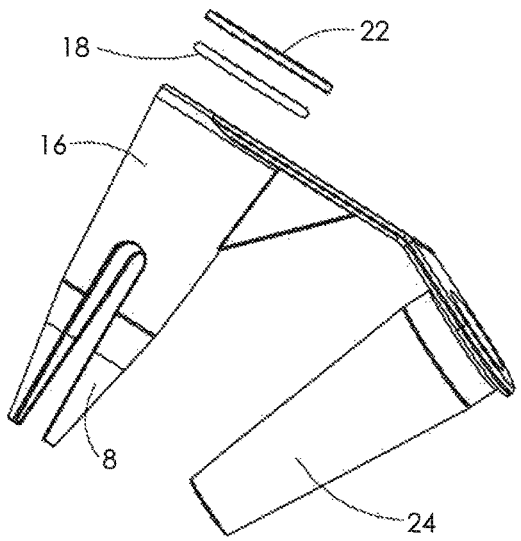
FIG. 14 is an exploded elevational view of the adapter assembly of the subject invention.
Figure 15:
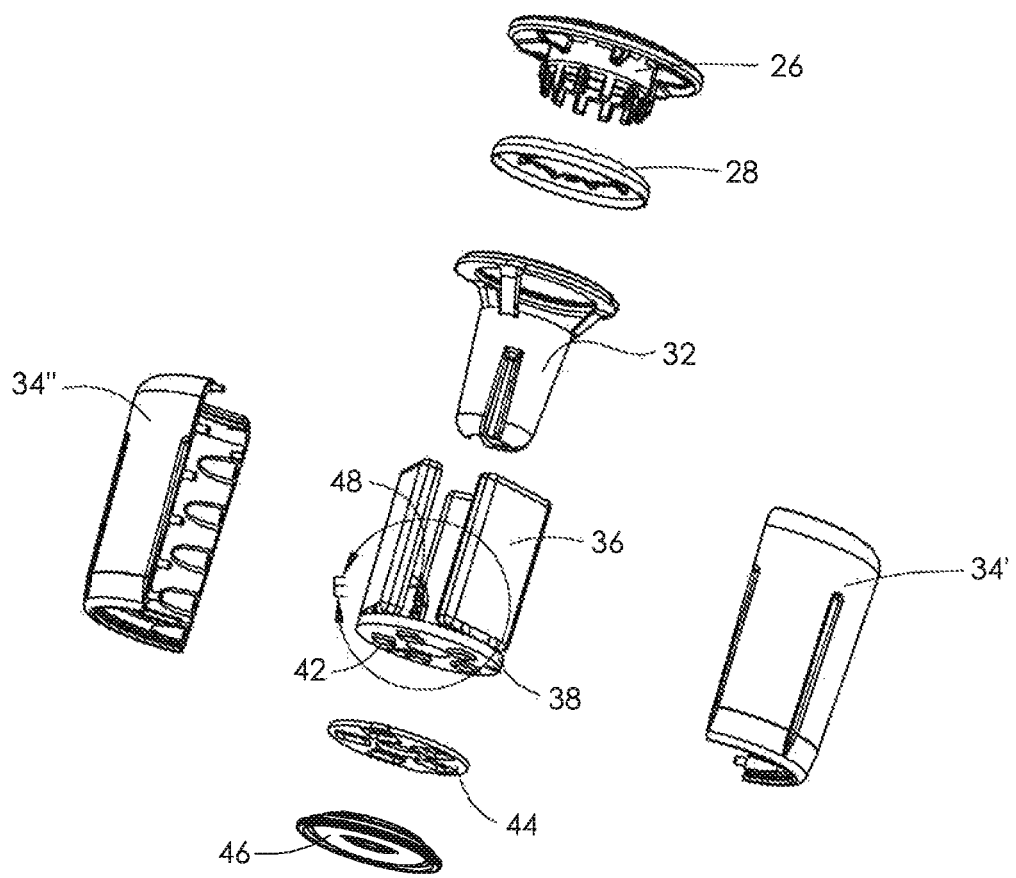
FIG. 15 is an exploded perspective view of the battery powered lighting device shown in FIGS. 1 and 2.
Figure 16:
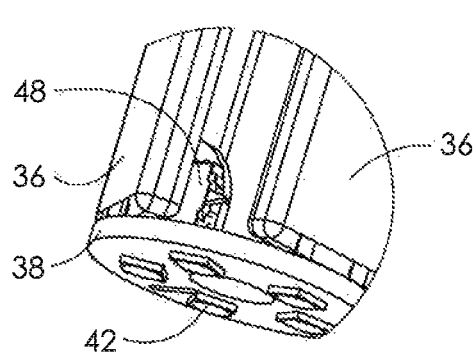
FIG. 16 is an enlarged localized view taken from FIG. 15.

Referring to FIGS. 3-9 and 14, the conical sleeve portion 16 of adapter assembly 30 is bifurcated so as to form flexible split conical sections 8 for engaging the distal end portion 14 of the surgical instrument 10. More particularly, the conical sections 8 of the sleeve portion 16 are adapted and configured to flexibly engage a proximal end portion 12 of the electrode blade 4, at a location that is proximal to a medial flange portion 6 thereof, as best seen in FIGS. 10 and 11. This enables greater compatibility with instruments of different size and/or geometry.

Figure 17:
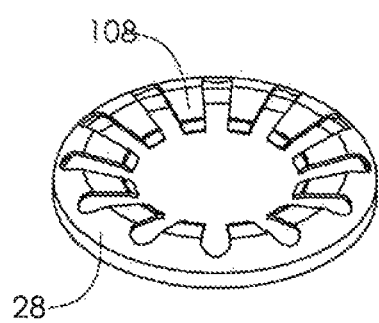
FIG. 17 is a perspective view of the jamming ring shown in FIG. 15.
Figure 18:
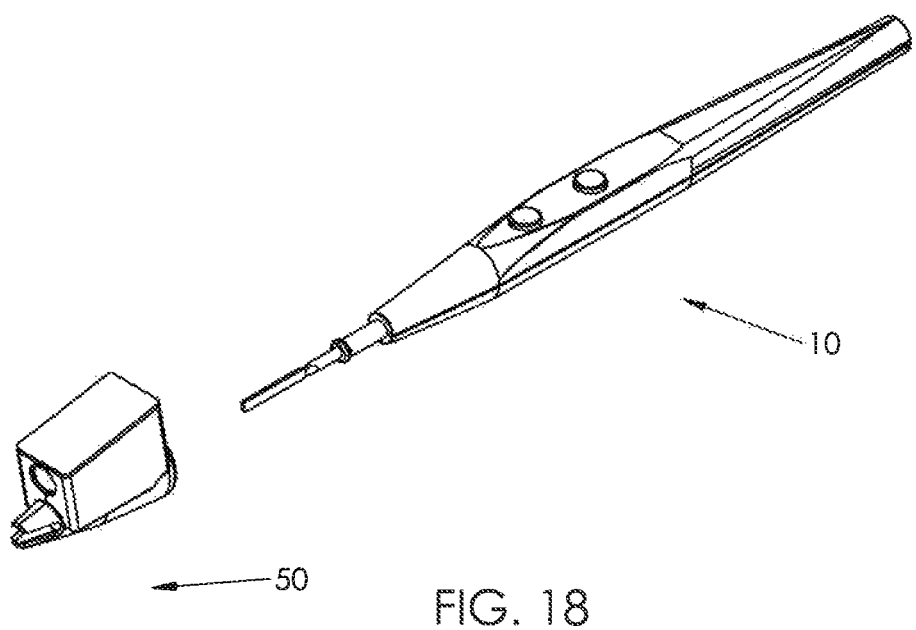
FIG. 18 is an exploded perspective view of a second embodiment of the adapter assembly of the subject invention, separated from the handheld electrosurgical instrument.
Figure 19:
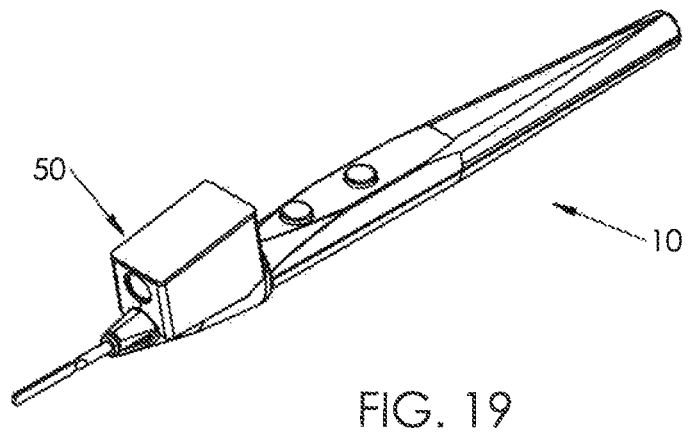
FIG. 19 is a perspective view of the adapter assembly of FIG. 18 engaged on the distal end portion of the handheld electrosurgical instrument.
Figure 20:
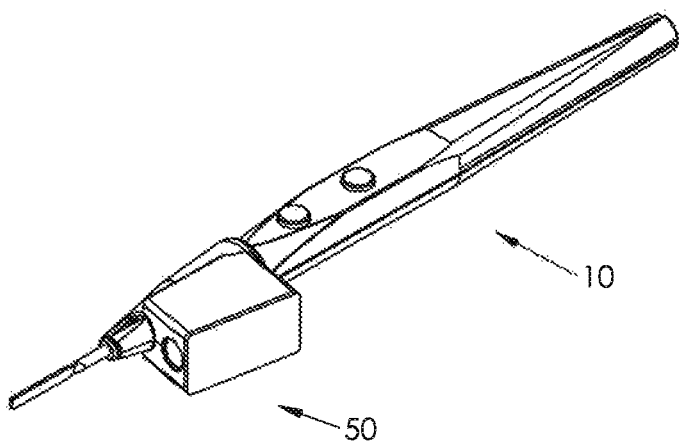
FIG. 20 illustrates the adapter assembly rotated 90 degrees from the position shown in FIG. 19, about the axis of handheld electrosurgical instrument.

As best seen in FIGS. 12 and 15-17, the conical shaft 24 is configured to engage a central bore of the lighting device 40. More particularly, the lighting device 40 consists of a two-part generally cylindrical body 34' and 34" that defines a cavity for supporting an interior body portion 32, which forms the central reception bore of the lighting device 40. A jamming ring 28, best seen in FIG. 17, is disposed at the proximal end of the lighting device 40, axially aligned with the central reception bore of the interior body portion 32 for frictionally engaging the conical shaft portion 24 of the adapter assembly 30. An end cap 26 retains the jamming ring 28 in the cylindrical body 34 of the lighting device 40.

The interior cavity of the body of the lighting device 40 also supports a PC board 38 that includes a plurality of circumferentially arranged LED or other light sources 42, at least one or a plurality of batteries 36 for energizing the light sources 42 and a switching mechanism 48 for activating the light sources 42 upon engagement of the lighting device 40 on the conical shaft 24 of the adapter assembly 30. An annular lens 46 covers the light sources 42 to and a spacer 44 is disposed between the light sources 42 on the PC board 38 and the lens 46.

The circumferentially arranged light sources 42 and the annual lens 46 defines the illumination axis of the lighting device 40, which angularly intersects the central axis of the surgical instrument 10 when the lighting device 40 is engaged on the conical shaft portion 24 of the adapter assembly 30 and the conical sleeve portion 16 is engaged on the distal end portion of the surgical instrument 10.

Figure 5:
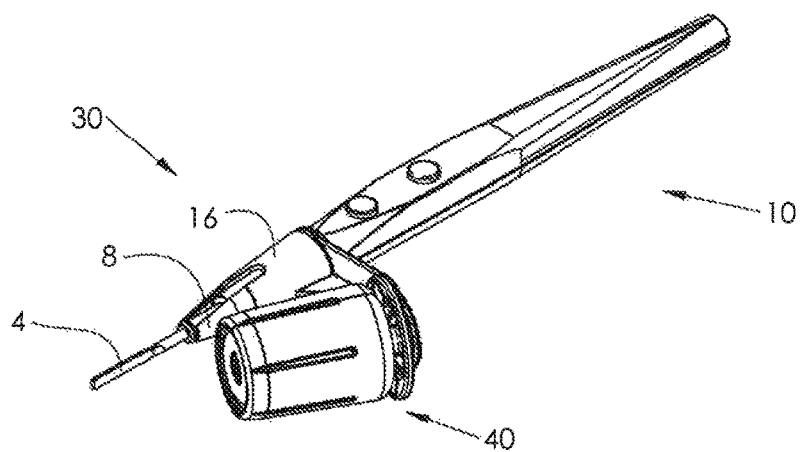
FIG. 5 is perspective view of the first body portion of the adapter assembly of the subject invention engaged on the distal end portion of the handheld electrosurgical instrument, with the lighting device attached to the second body portion of the adapter assembly.
Figures 6, 7, 8, 9, 10:
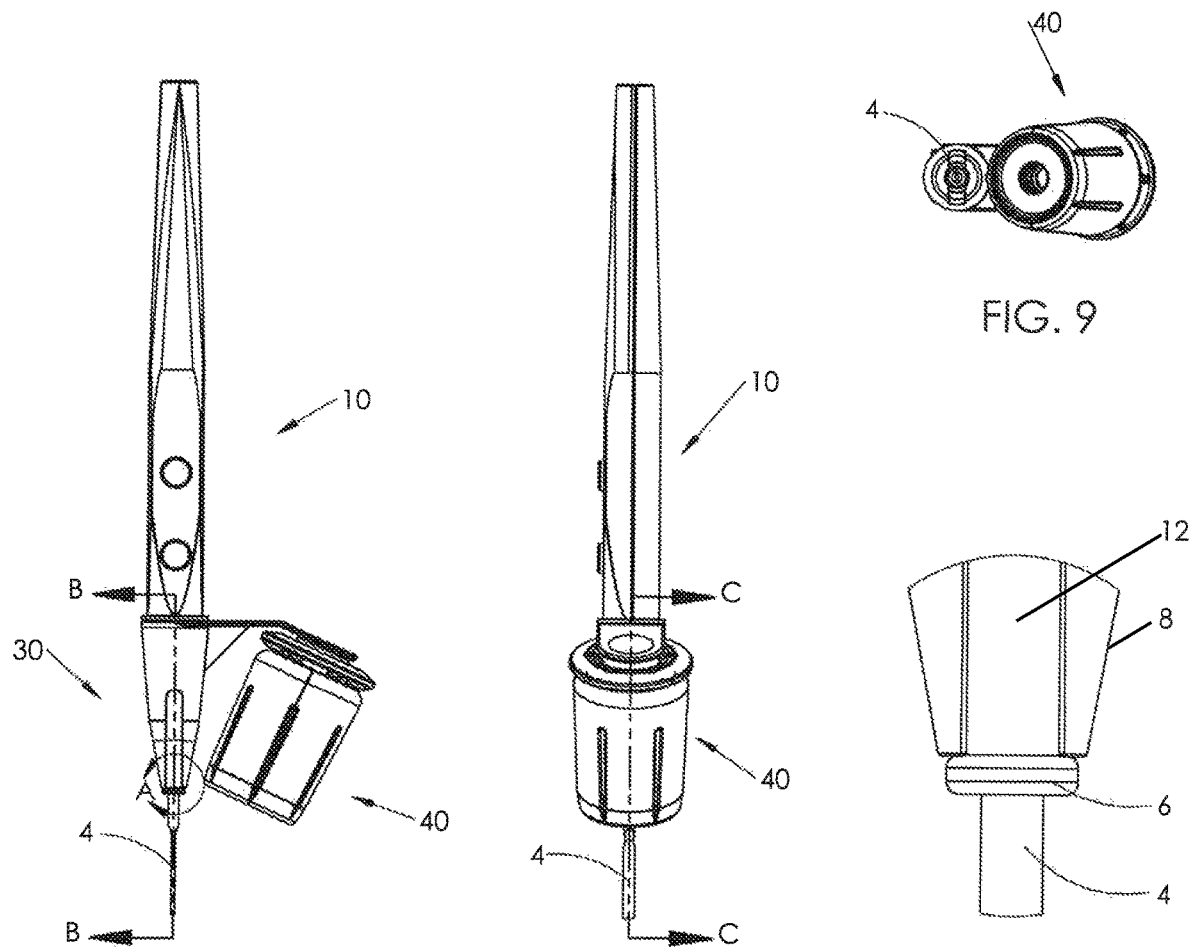
FIG. 6 illustrates the adapter assembly rotated 90 degrees from the positon shown in FIG. 5, about the axis of handheld electrosurgical instrument.
FIG. 7 is a side elevational view of the adapter assembly and lighting device mounted on the distal end portion of the handheld electrosurgical instrument.
FIG. 8 is a top plan view of the adapter assembly and lighting device mounted on the distal end portion of the handheld electrosurgical instrument.
FIG. 9 is a front end view of the adapter assembly and lighting device mounted on the distal end portion of the handheld electrosurgical instrument.
FIG. 10 is an enlarged localized view taken from FIG. 7.

It can be seen by comparing FIG. 5 to FIG. 6, that the conical sleeve portion 16 of adapter assembly 30 is configured to facilitate axial rotation of the adapter assembly 30 and hence the lighting device 40, about the central axis of the surgical instrument 10. This enables the user to preserve their line of sight or move the illumination axis if they are in an area of the anatomy that is difficult to access. In this regard, as best seen in FIGS. 11-14, a resilient O-ring 18 is positioned within the interior bore of the conical sleeve portion 16 and it is held in place by an end cap 22 for frictionally engaging the distal end portion 14 of the surgical instrument 10 and thereby prevent unwanted axial rotation of the conical sleeve portion 16 without the application of a rotational force thereto.

Referring now to FIGS. 18-36, there is illustrated another adapter assembly 50 for attaching a lighting device to a handheld surgical instrument 10 at a location that is adjacent to a distal end portion 14 of the surgical instrument 10, and is configured in such a manner so that a illumination axis of the lighting device angularly intersect a central axis of the surgical instrument 10.

Figure 26:
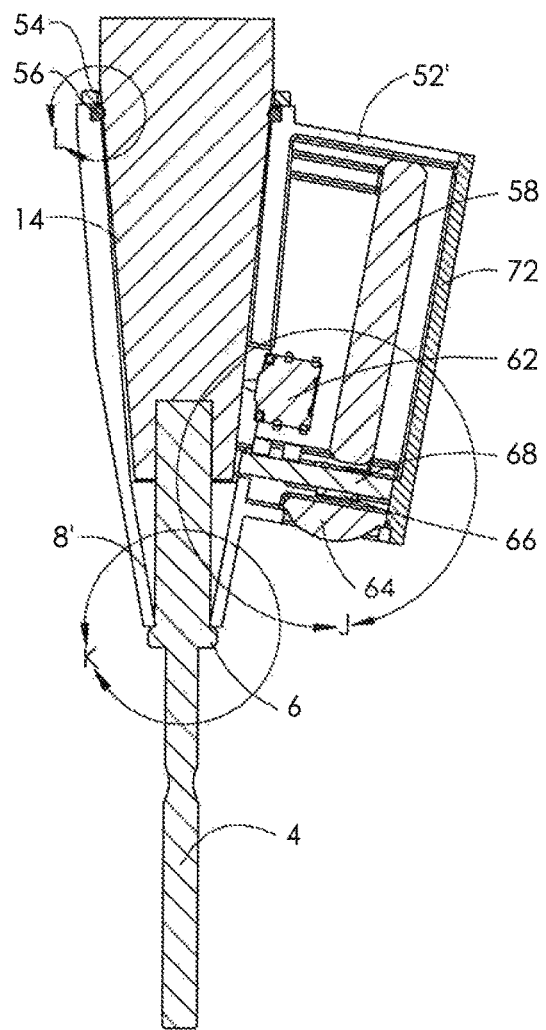
FIG. 26 is a cross-sectional view taken along line H-H of FIG. 21.
Figure 27:
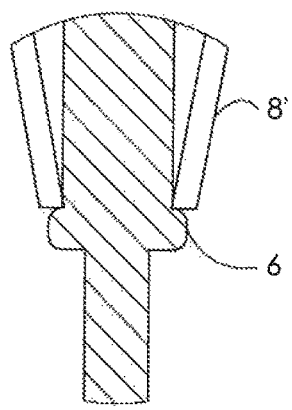
FIG. 27 is an enlarged localized view of the distal end portion of the surgical instrument and the electrode blade taken from FIG. 26.
Figure 28:
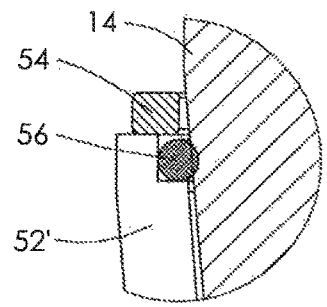
FIG. 28 is an enlarged localized view of a proximal end portion of the first body portion of the adapter assembly taken from FIG. 26.
Figure 29:
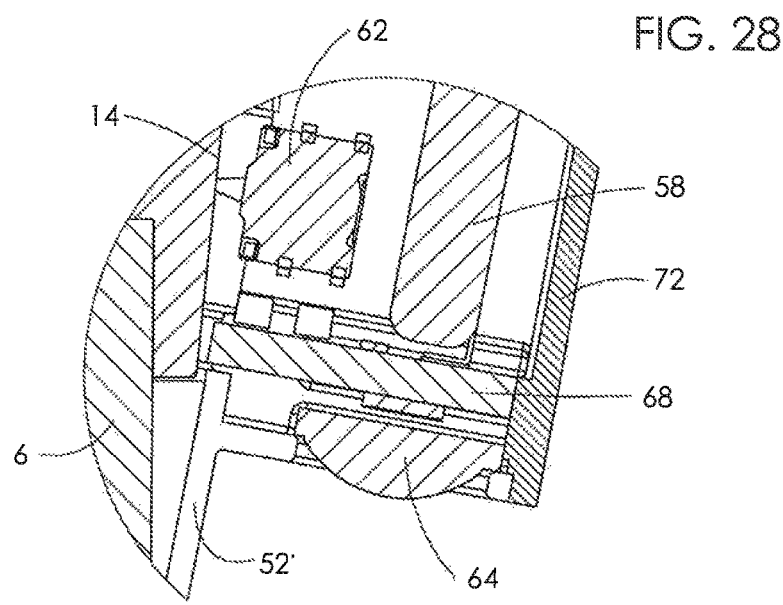
FIG. 29 is an enlarged localized view of a distal end portion of the second body portion of the adapter assembly taken from FIG. 26.
Figure 30:
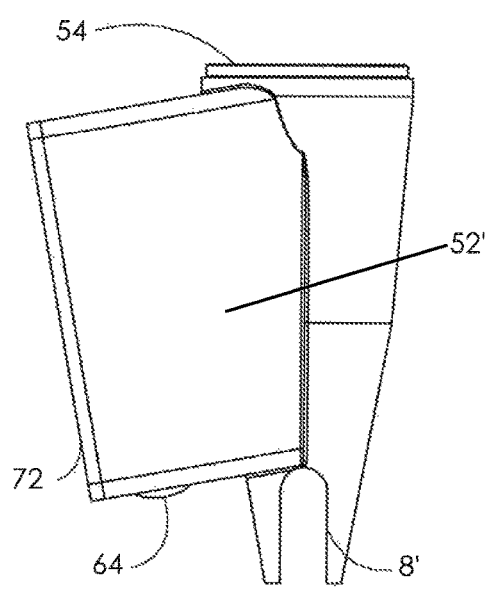
FIG. 30 is a side elevational view of the adapter assembly of FIG. 18.
Figure 31:
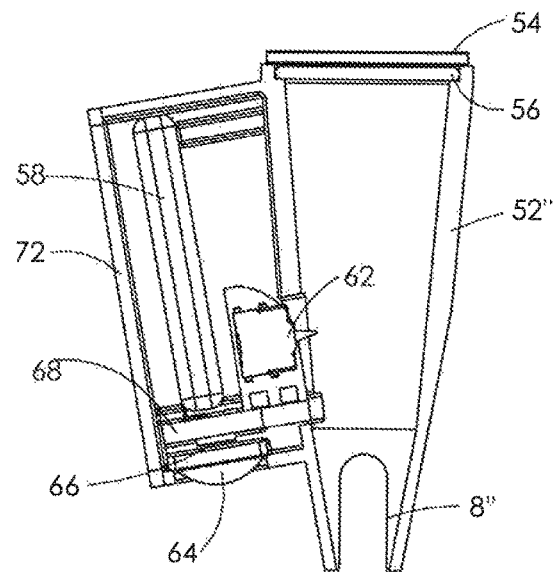
FIG. 31 is a cross-section view taken from FIG. 30.
Figure 32:
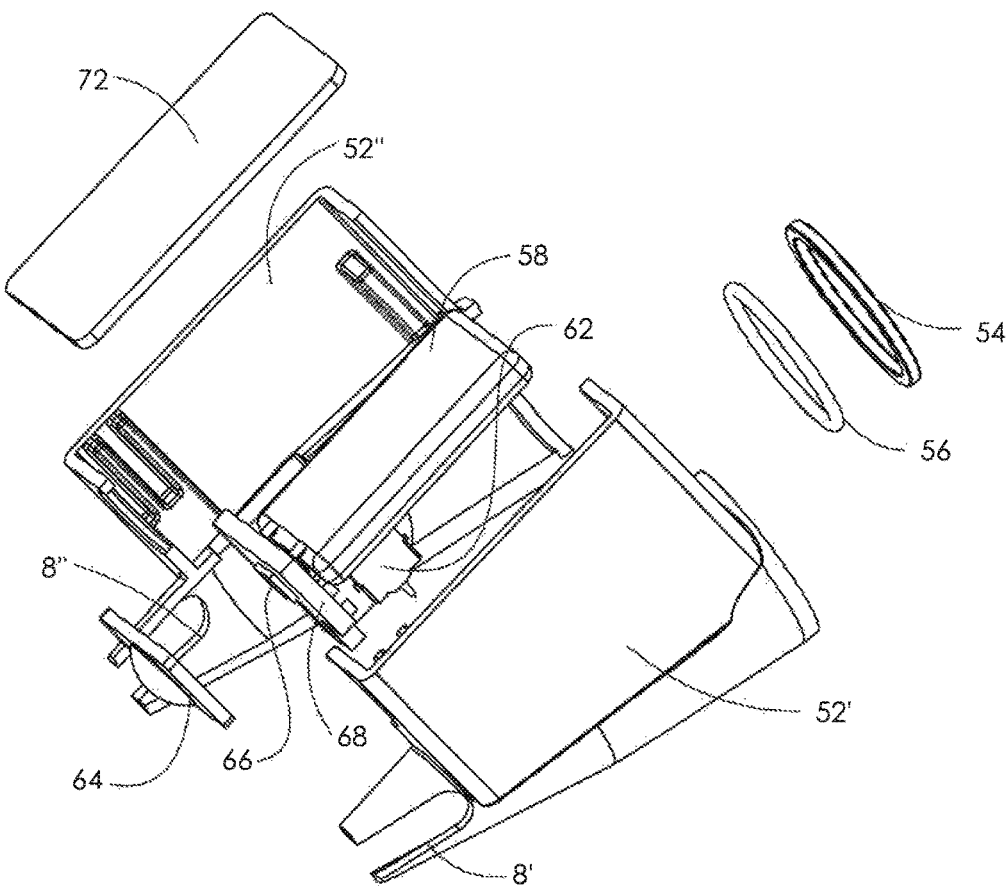
FIG. 32 is an exploded perspective view of the adapter assembly shown in FIG. 30.
Figure 33:
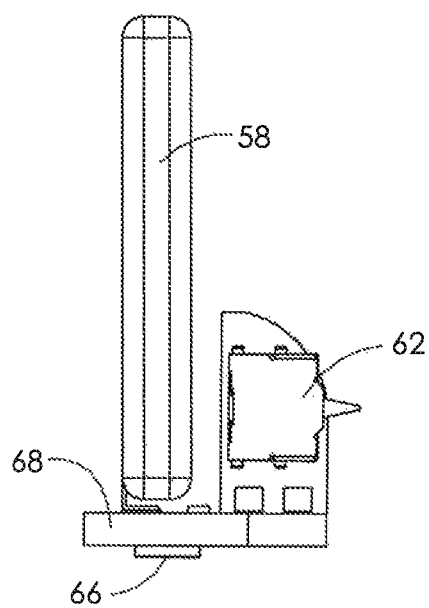
FIG. 33 is a is a side elevational view of the PCB assembly housed in the adapter assembly shown in FIG. 32.
Figure 34:
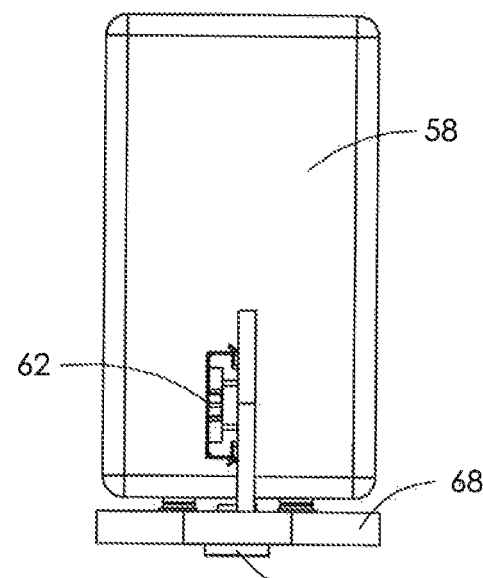
FIG. 34 is a is a plan view of the PCB assembly shown in FIG. 32.
Figure 35:
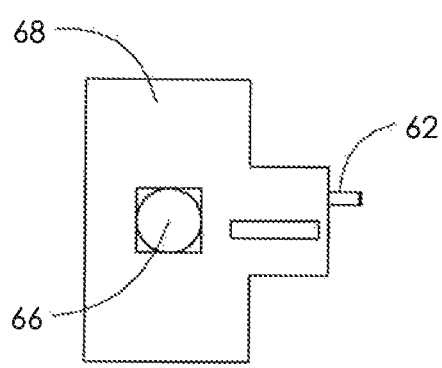
FIG. 35 is a front end view of the PCB assembly shown in FIG. 32.
Figure 36:
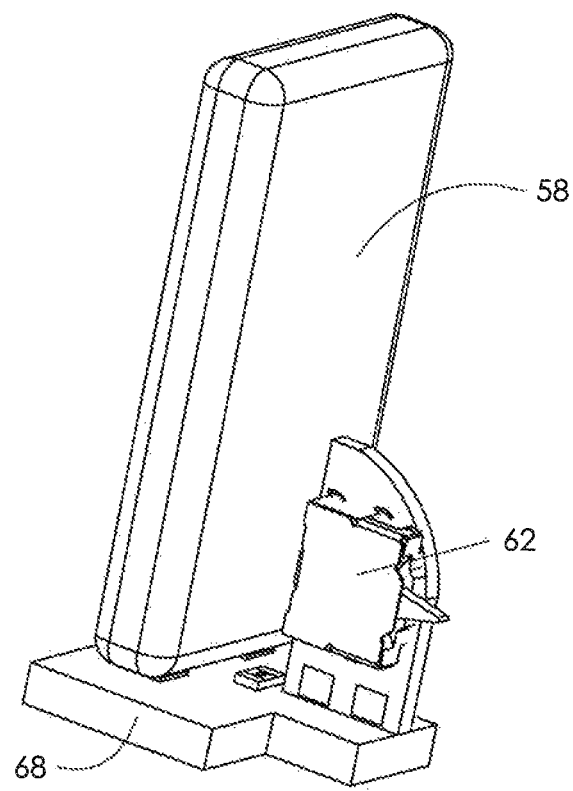
FIG. 36 is a perspective view of the PCB assembly shown in FIG. 32.
Figure 37:
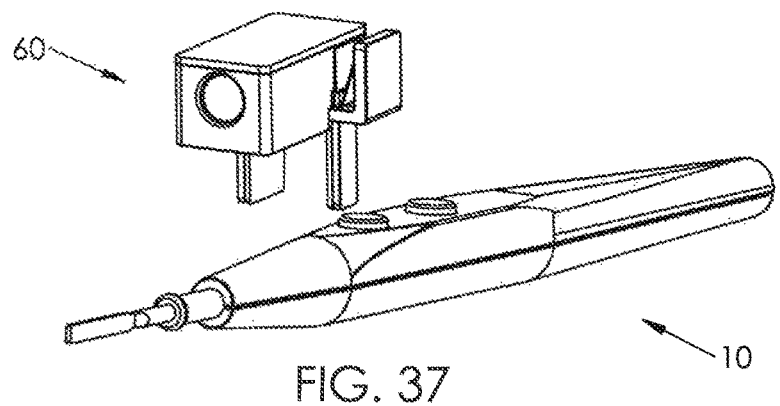
FIG. 37 is an exploded perspective view of a third embodiment of the adapter assembly of the subject invention, separated from the lighting device and the handheld electrosurgical instrument.
Figure 38:
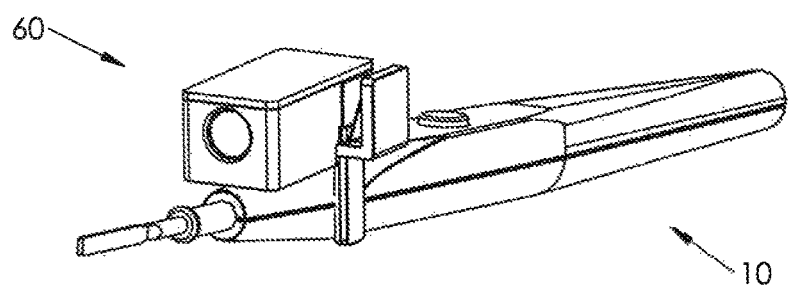
FIG. 38 is perspective view of the adapter assembly of FIG. 37 engaged on the distal end portion of the handheld electrosurgical instrument.
Figure 39:
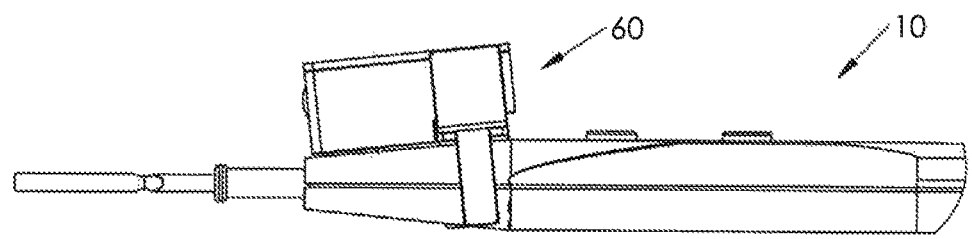
FIG. 39 is a side elevational view of the adapter assembly of FIG. 37 engaged on the distal end portion of the handheld electrosurgical instrument.
Figure 40:
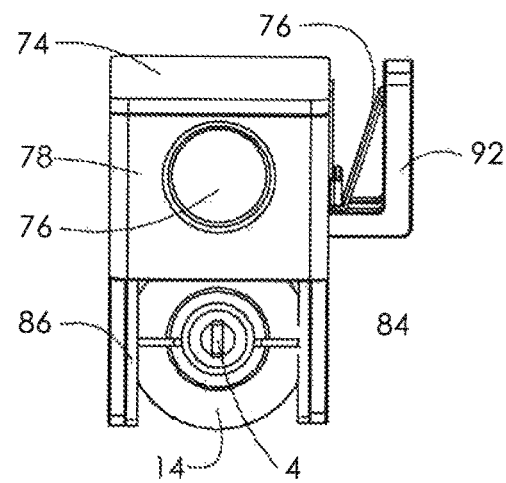
FIG. 40 is a front end view of the adapter assembly of FIG. 37 attached on the distal end portion of the handheld electrosurgical instrument.
Figure 41:
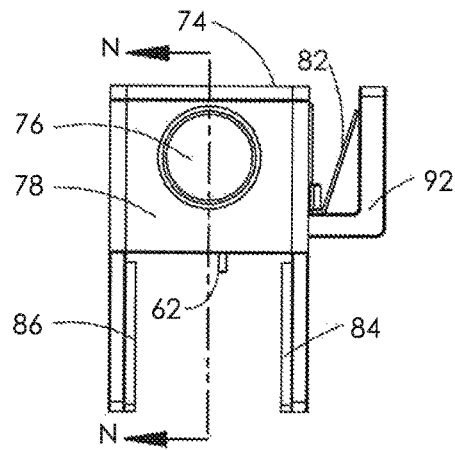
FIG. 41 is a front end view of the adapter assembly of FIG. 37.
Figure 42:
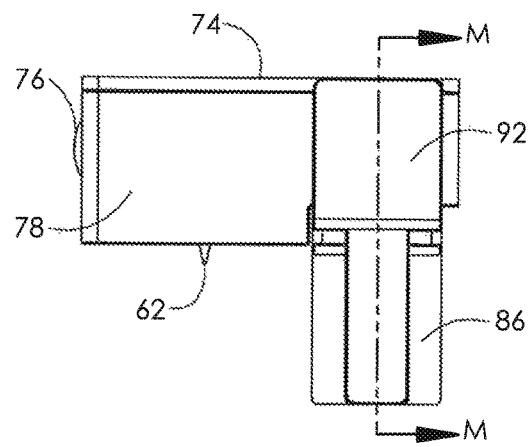
FIG. 42 is a side elevational view of the adapter assembly of FIG. 37.
Figure 43:
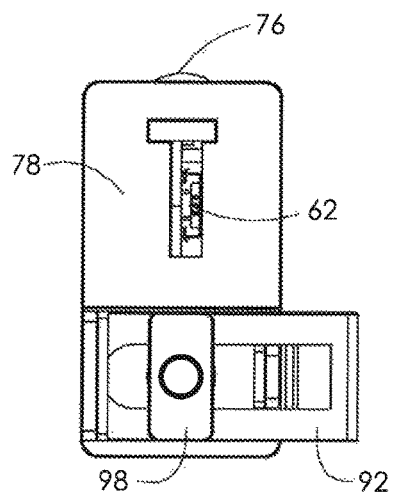
FIG. 43 is a bottom plan view of the adapter assembly of FIG. 37.
Figure 44:
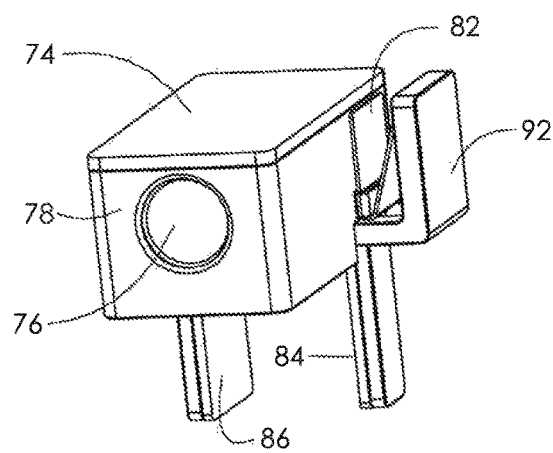
FIG. 44 is a perspective view of the adapter assembly of FIG. 37.
Figure 45:
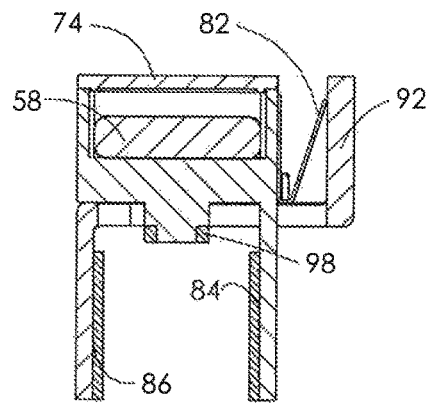
FIG. 45 is a cross-sectional view taken along line M-M of FIG. 42.
Figure 46:
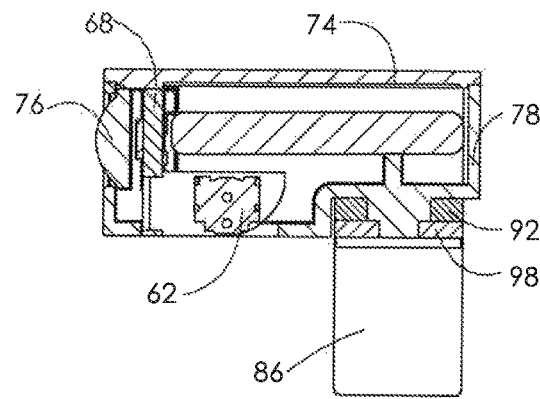
FIG. 46 is a cross-sectional view taken along line N-N of FIG. 41.
Figure 47:
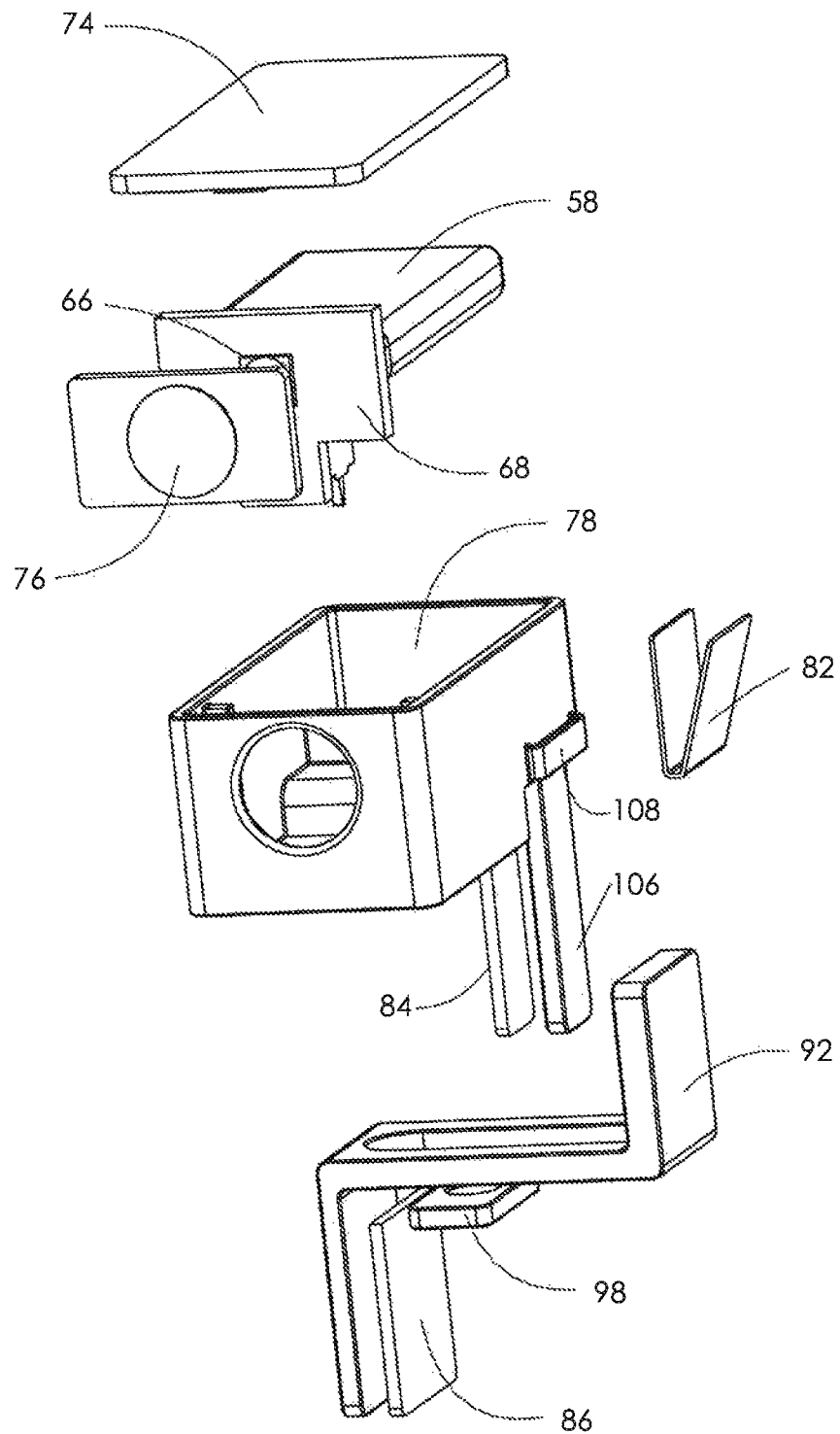
FIG. 47 is an exploded perspective view of the adapter assembly of FIG. 37.

The adapter assembly 50 includes a conical sleeve portion 52 (52' and 52"), similar to the conical sleeve portion 16 of adapter assembly 30, in that it includes a bifurcated tip portion 8' and 8" and an interior bore configured to engage a distal end portion 14 of the surgical instrument 10 at a position along a central axis thereof, as best seen in FIGS. 26 and 27. The conical sleeve portion 52 is configured to facilitate axial rotation of the adapter assembly 50 about the central axis of the surgical instrument 10. In this regard, as best seen in FIGS. 26 and 28, a resilient O-ring 56 is positioned within the interior bore of the conical sleeve portion 52 and it is held in place by an end cap 56 for frictionally engaging the distal end portion 14 of the surgical instrument 10 and thereby prevent unwanted axial rotation of the conical sleeve portion 52 without the application of a rotational force thereto.

Referring to FIGS. 26 and 29-36, the adapter assembly 50 further includes a housing portion 72 formed integral with and extending radially outwardly from the conical sleeve portion 52. The housing portion 72 has a cover enclosing an interior chamber for supporting the lighting device of adapter assembly 50. The lighting device includes an LED or other light source 66 associated with a PC board 68, a battery 58 for energizing the light source 66, a switching mechanism 62 for activating the light source 66 when the distal end portion 14 of the surgical instrument 10 is engaged in the conical sleeve portion 52, and a circular lens 64.

The light source 66 and lens 64 are located at a distal end of the housing portion 72 and together they define the illumination axis of the lighting device of adapter assembly 50. As best seen in FIG. 26, the orientation of the housing portion 72 is such that the illumination axis that is defined by the light source 66 and lens 64 angularly intersects a central axis of the surgical instrument 10.

Referring now to FIGS. 37-53, there is illustrated another adapter assembly 60 for attaching a lighting device to a handheld surgical instrument 10 at a location that is adjacent to a distal end portion 14 of the surgical instrument 10, and is configured in such a manner so that an illumination axis of the lighting device angularly intersect a central axis of the surgical instrument 10.

The adapter assembly 60 includes a housing potion 78 having a cover 74 enclosing an interior chamber for supporting the lighting device, which includes an LED or other light source 66 mounted on a PC board 68, a battery 58 for energizing the light source 66, a switching mechanism 62 for activating the light source 66 and a circular lens 76 located at a distal end of the housing 78 to define the illumination axis of the lighting device.

The adapter assembly 60 further includes a clamping mechanism that is operatively associated with the housing portion 78 for engaging the distal end portion 14 of a surgical instrument 10 in such a manner so that the illumination axis of the lighting device angularly intersects the central axis of the surgical instrument 10. The clamping mechanism includes a movable flange portion 92 (see FIG. 52) and a fixed flange portion 106 (see FIG. 53). The movable flange portion 92 has a longitudinal slot 102 for accommodating a guide boss 104 extending from the bottom of housing 78, which is retained by a cap 98.

Figure 48:
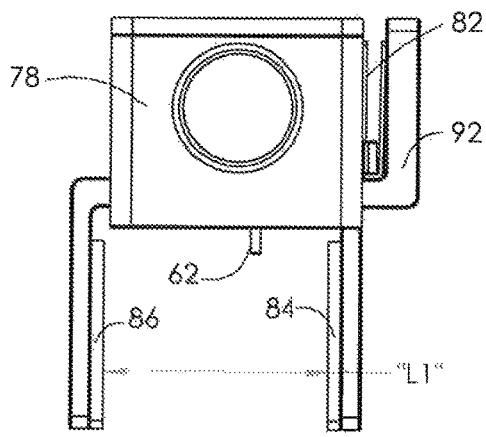
FIG. 48 is a front end view of the adapter assembly of FIG. 37 with the clamping mechanism disposed in an open position.
Figure 49:
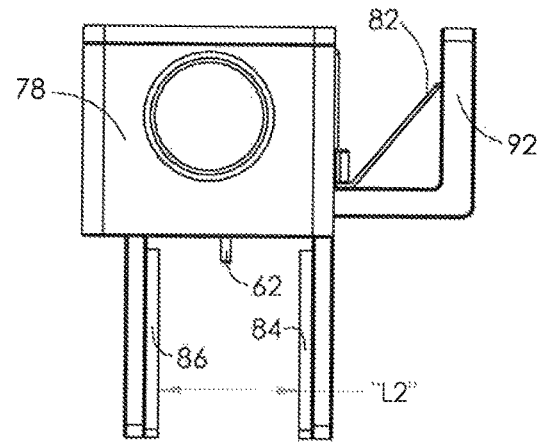
FIG. 49 is a side elevational view of the adapter assembly of FIG. 37 with the clamping mechanism disposed in a closed position.
Figure 50:
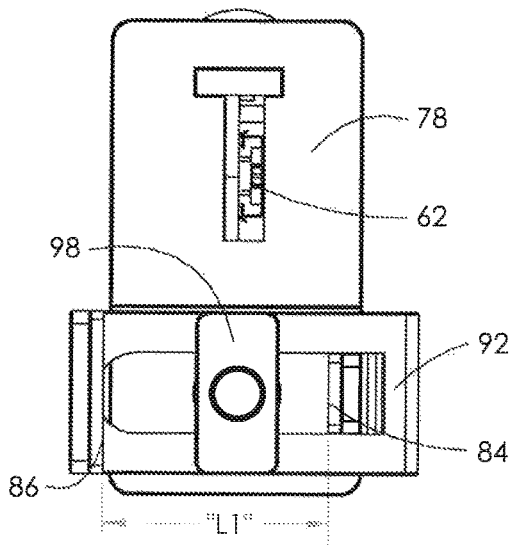
FIG. 50 is a bottom plan view of the adapter assembly of FIG. 37 with the clamping mechanism disposed in an open position.
Figure 51:
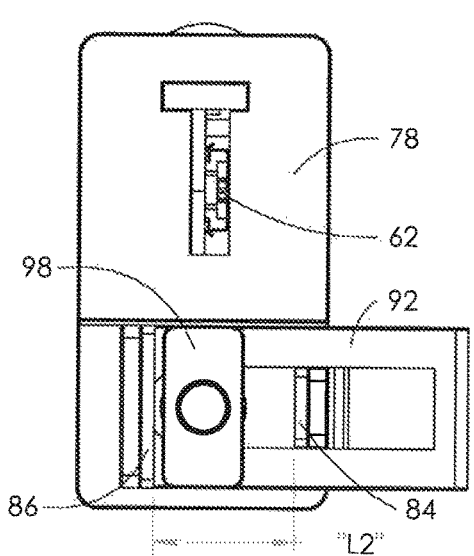
FIG. 51 is a bottom plan view of the adapter assembly of FIG. 37 with the clamping mechanism disposed in a closed position.
Figure 52:
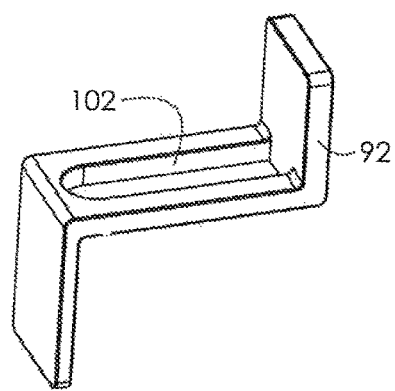
FIG. 52 is a perspective view of a movable portion of the clamping mechanism.
Figure 53:
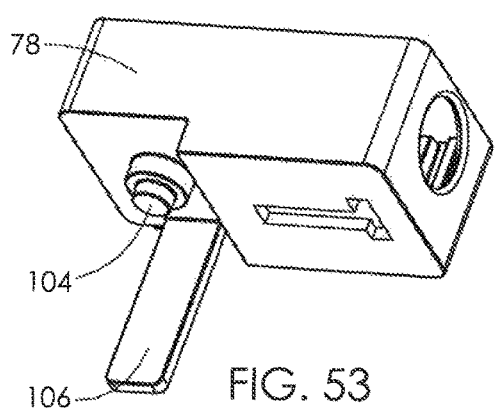
FIG. 53 is a perspective view of the housing portion of the adapter assembly with the movable portion of the clamping mechanism separated therefrom.
Figure 54:
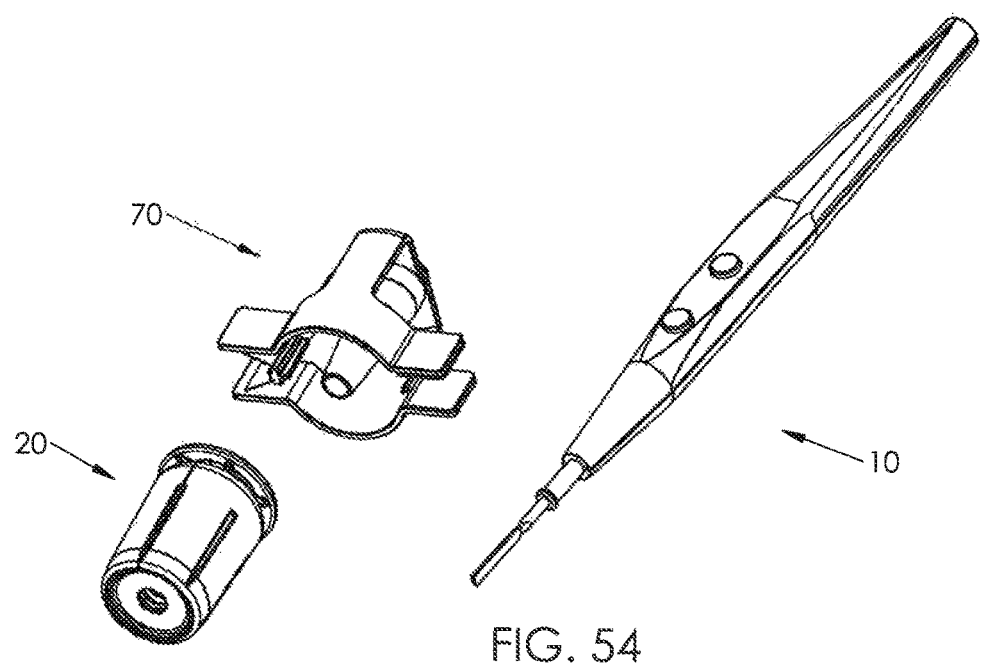
FIG. 54 is an exploded perspective view of a fourth embodiment of the adapter assembly of the subject invention, separated from the lighting device and the handheld electrosurgical instrument.
Figure 55:
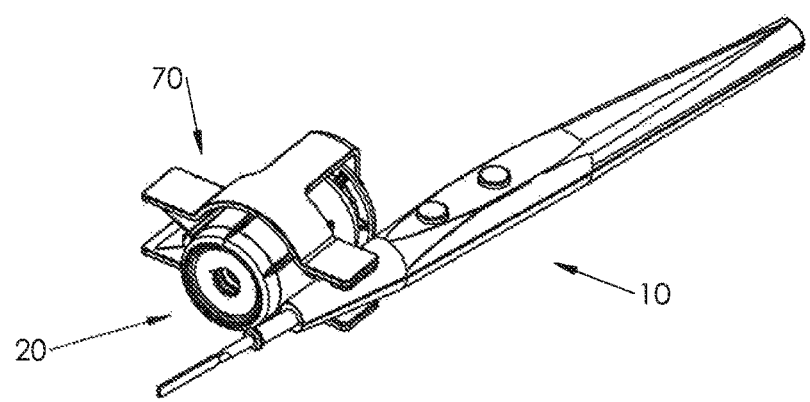
FIG. 55 is perspective view of a lighting device engaged within the adapter assembly shown in FIG. 54 and with the adapter assembly engaged on the distal end portion of the handheld electrosurgical instrument.
Figure 56:
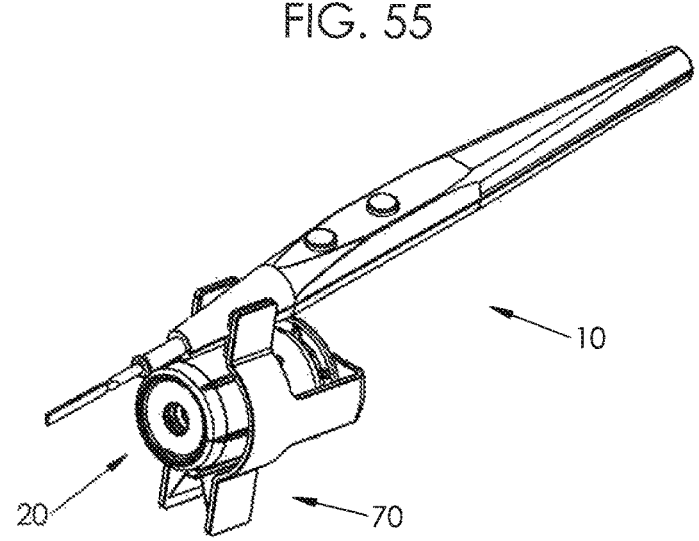
FIG. 56 illustrates the adapter assembly rotated 90 degrees from the position shown in FIG. 55, about the axis of handheld electrosurgical instrument, whereby the bulk of the device/adaptor is readily removed from the surgeon's line of sight while maintaining the intersection between the instrument axis and the illumination axis.
Figure 61:
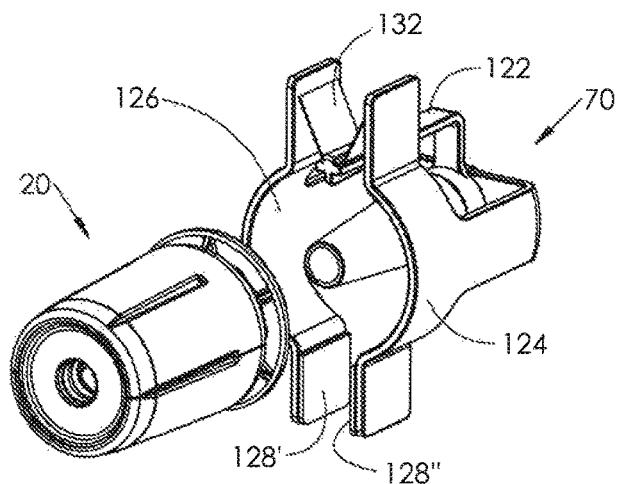
FIG. 61 is an exploded perspective view of the lighting device separated from the adapter assembly of FIG. 54.
Figure 62:
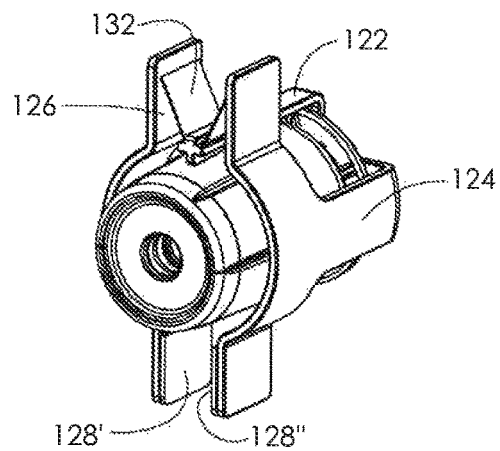
FIG. 62 is a perspective view of the lighting device engaged with the adapter assembly of FIG. 54.
Figure 63:
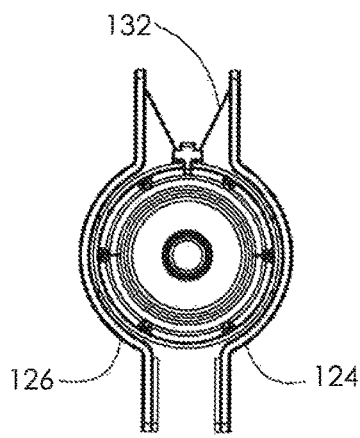
FIG. 63 is a front end view of the lighting device engaged with the adapter assembly as shown in FIG. 62.
Figure 64:
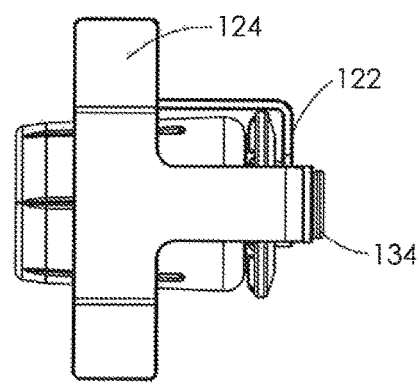
FIG. 64 is a side elevational view of the lighting device engaged with the adapter assembly as shown in FIG. 62.

Flange portion 92 is adapted and configured for linear movement relative to fixed flange portion 106 between an open position shown in FIGS. 48 and 50 for receiving the distal end portion 14 of the surgical instrument 10 and a closed position shown in FIGS. 49 and 51 for engaging the distal end portion 14 of the surgical instrument 10 at a position along a central axis thereof. A leaf spring 82 biases the movable flange portion 92 into the closed positon of FIGS. 49 and 51. And each engagement flange is provided with an elastomeric plate 84, 86 on interior surface thereof for engaging the distal end portion 14 of the surgical instrument 10. It should be appreciated that the elastomeric plates 84, 86 advantageously increase the compatibility of the adapter assembly 60, so that it can be used with surgical devices and instruments of varying shape and size, including those that have a rounded configuration as well as those that have a somewhat boxy configuration.

The switching mechanism 62 projects through an opening in the bottom of housing portion 78 and it is positioned to activate the light source 66 in housing 78 upon engagement of the distal end portion 14 of the surgical instrument 10 within the clamping mechanism of adapter assembly 60.

Referring now to FIGS. 54-70, there is illustrated another adapter assembly 70 for attaching a lighting device 20 (see FIGS. 15-17) to a handheld surgical instrument 10 at a location that is adjacent to a distal end portion 14 of the surgical instrument 10, and is configured in such a manner so that a illumination axis of the lighting device 20 angularly intersect a central axis of the surgical instrument 10.

Figure 65:
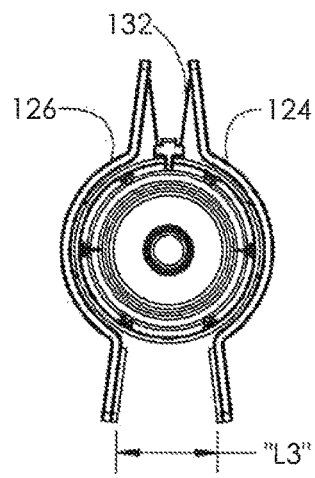
FIG. 65 is a front end view of the lighting device engaged with the adapter assembly as shown in FIG. 62 with the clamping mechanism in an open position.
Figure 66:
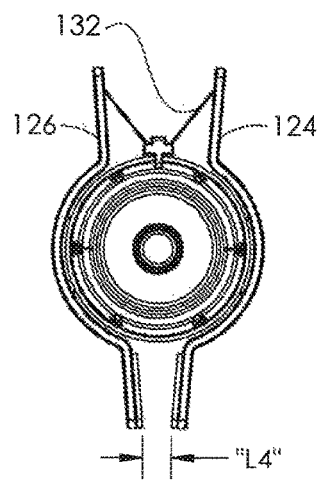
FIG. 66 is a front end view of the lighting device engaged with the adapter assembly as shown in FIG. 62 with the clamping mechanism in a closed position.
Figure 67:
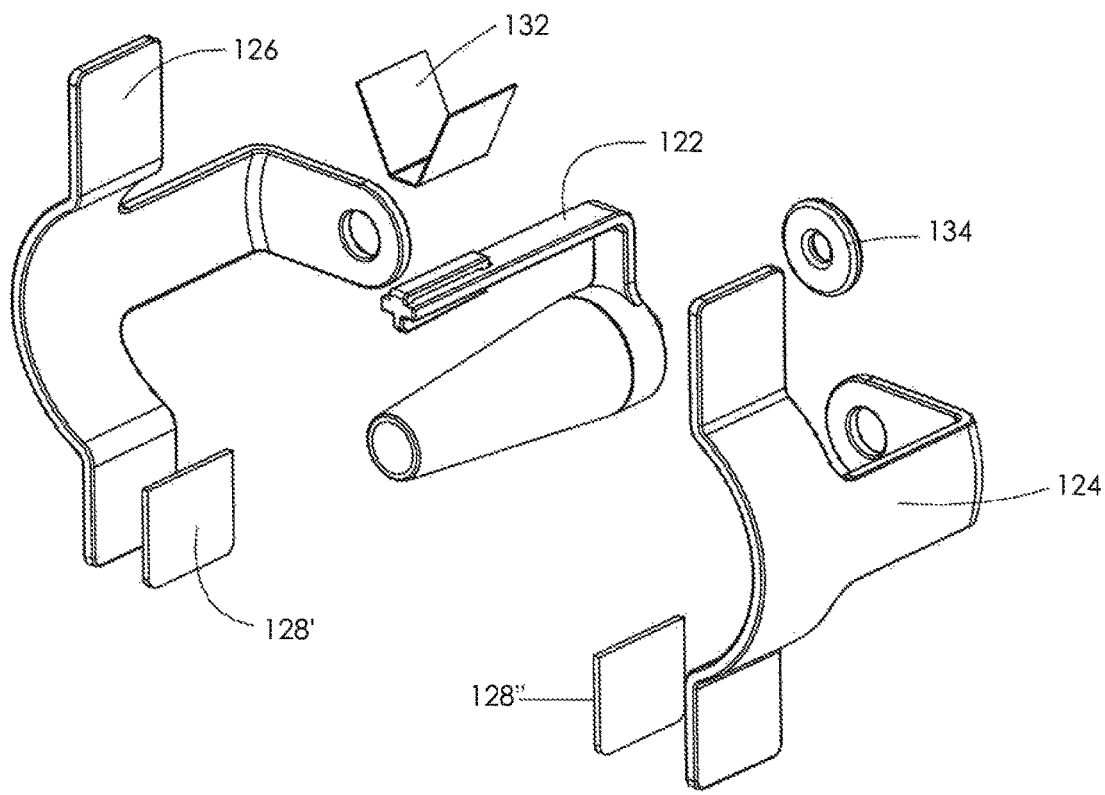
FIG. 67 is an exploded perspective view of the adapter assembly of FIG. 54.
Figure 68:
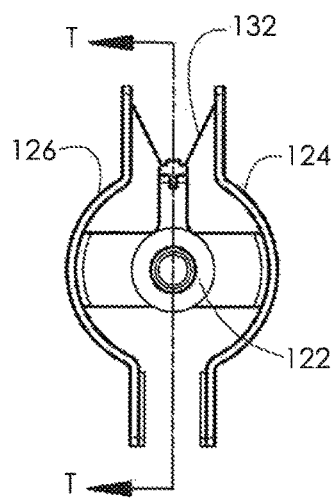
FIG. 68 is a front end view of the adapter assembly of FIG. 54.
Figure 69:
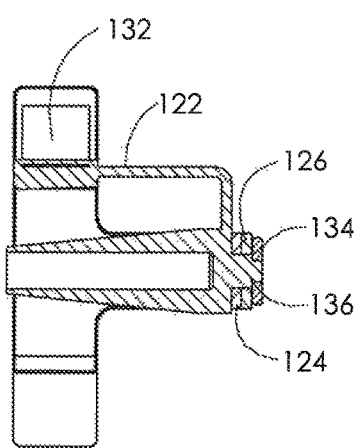
FIG. 69 is a cross-sectional view taken along line T-T of FIG. 68.
Figure 70:
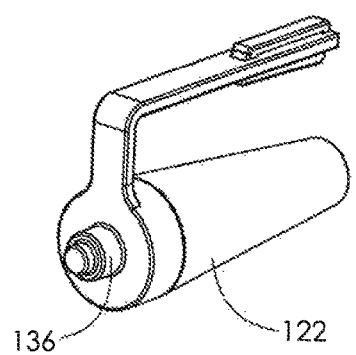
FIG. 70 is a perspective view of the conical shaft portion of the adapter assembly of FIG. 54, separated from the clamping mechanism thereof.
Figure 71:
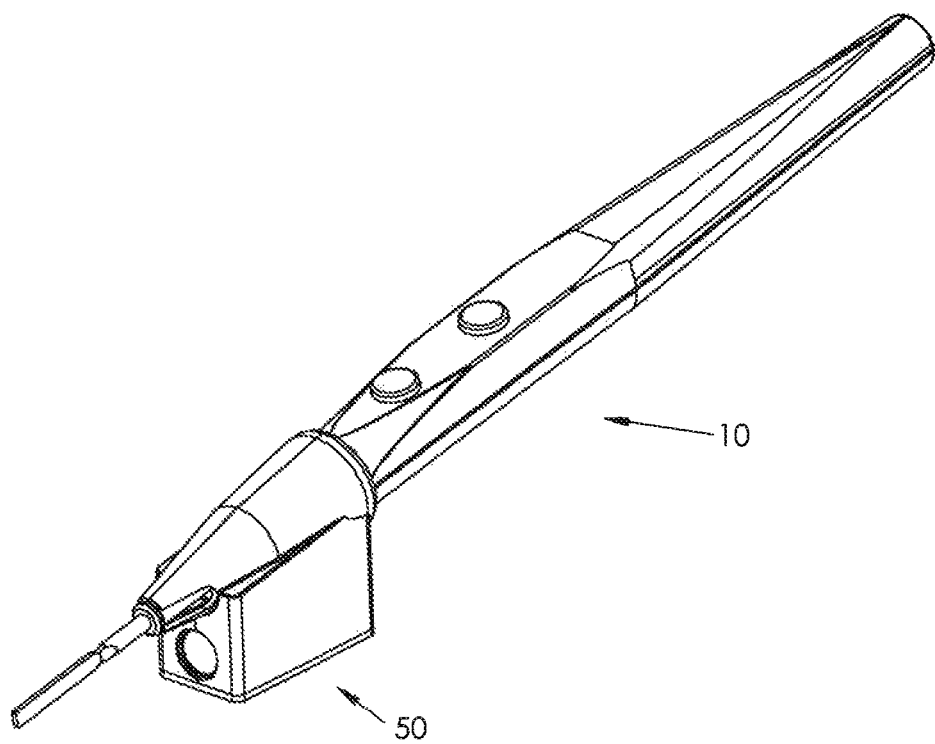
FIG. 71 is a perspective view similar to FIG. 19, with the adapter shown therein rotated 180 degrees.
Figure 72:
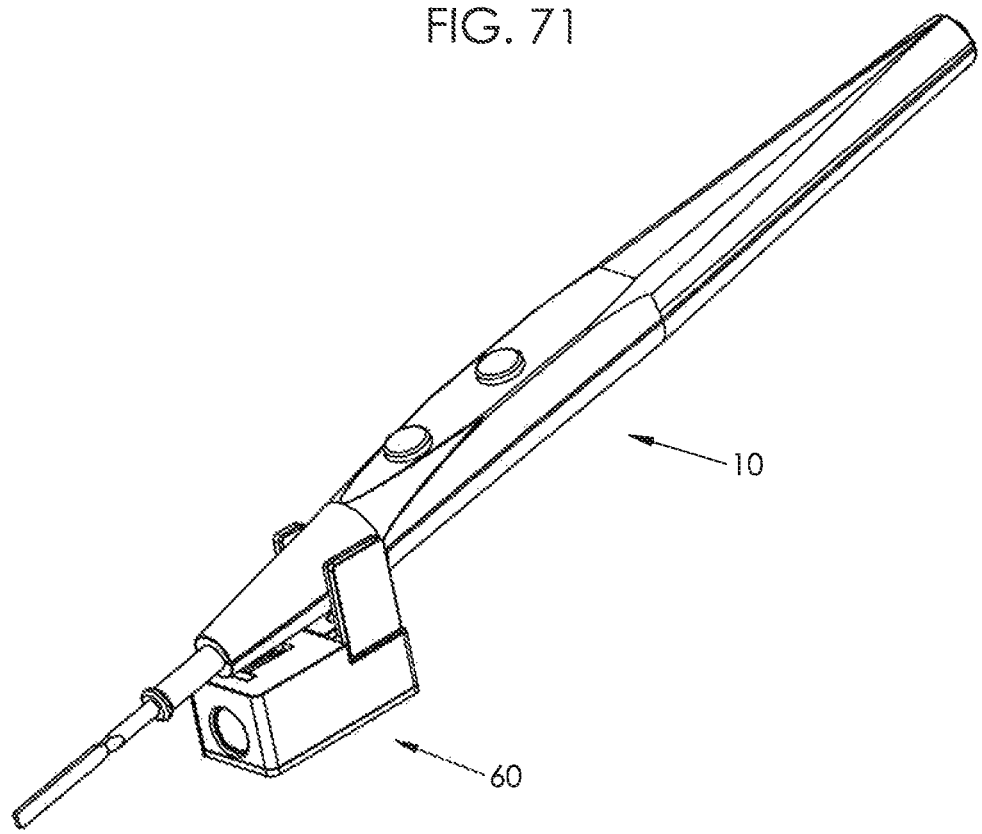
FIG. 72 is a perspective view similar to FIG. 38, with the adapter shown therein rotated 180 degrees.
Figure 73:
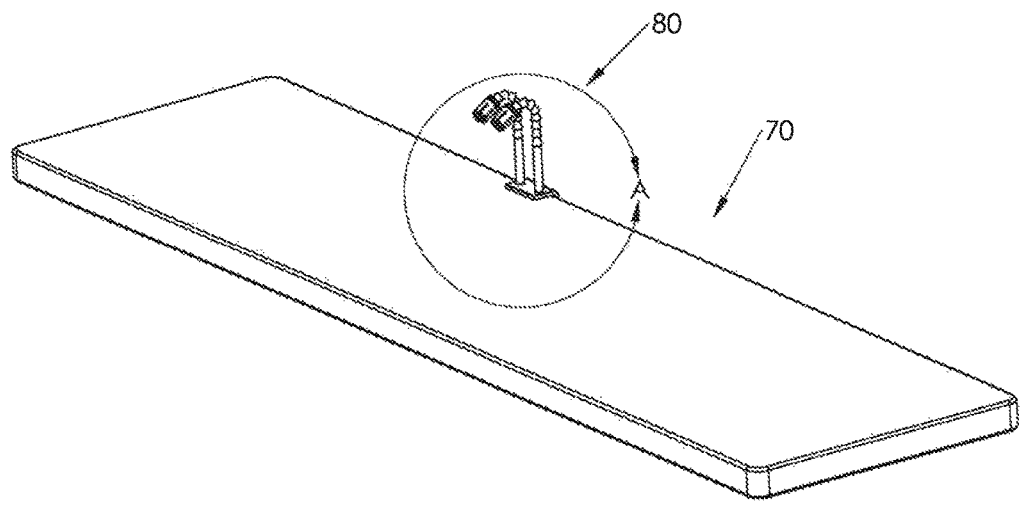
Figure 74:
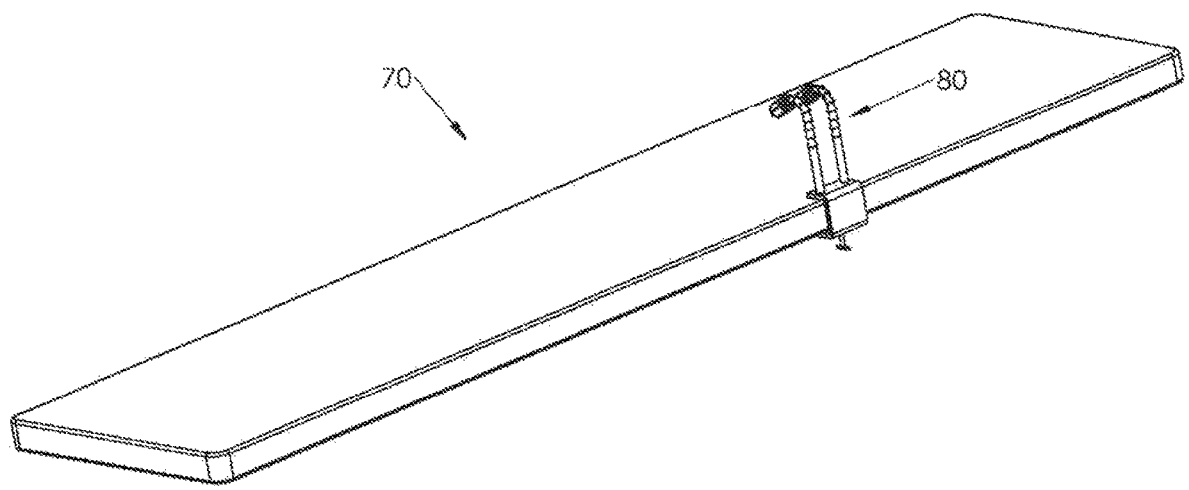
Figure 75:
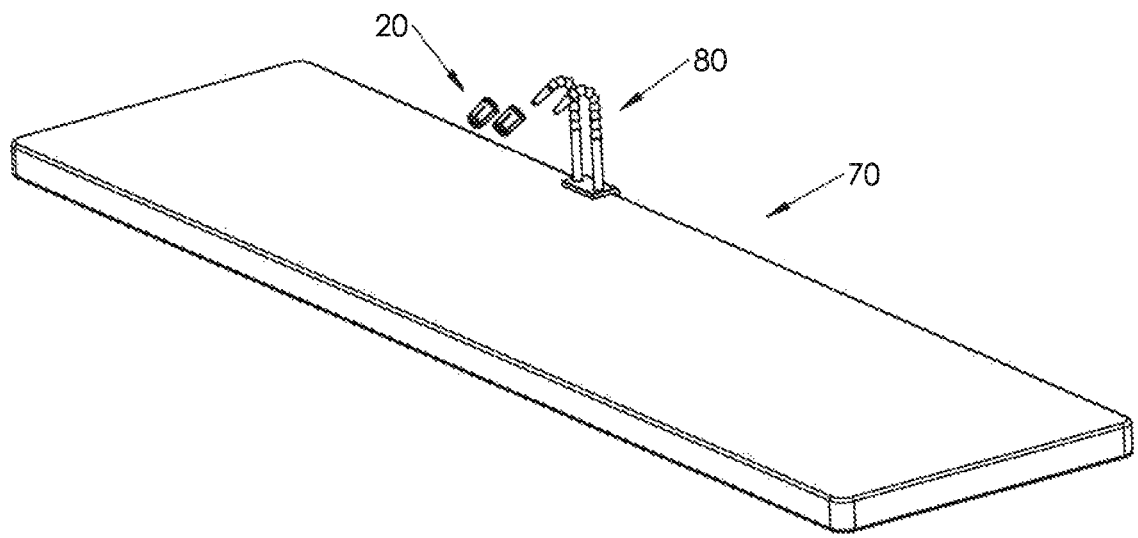
Figure 76:
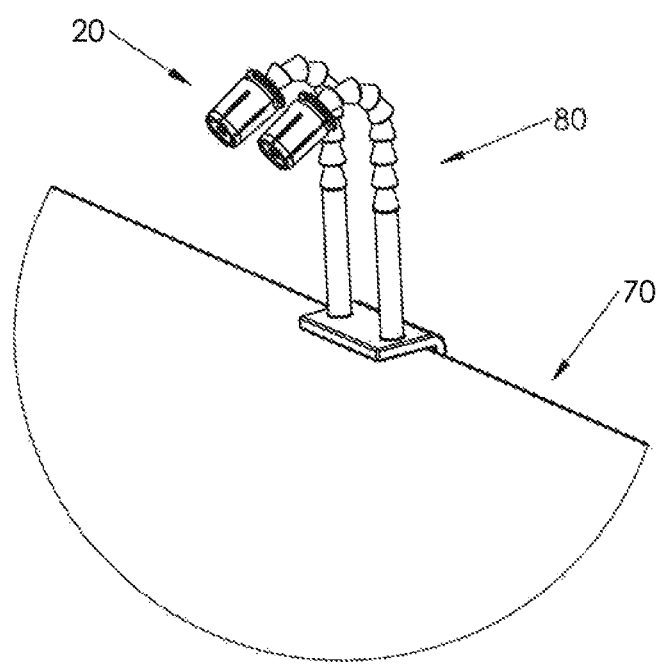

The adapter assembly 70 includes a conical shaft portion 122 configured to engage a central bore of the lighting device 20, as best seen in FIG. 60, and a clamping mechanism including a pair of spaced apart engagement flanges or arms 124 and 126 that are operatively associated with the conical shaft portion 122 and are adapted for pivotal movement between an open position shown in FIG. 65 for receiving the distal end portion 14 of the surgical instrument 10 and a closed position shown in FIG. 66 for engaging the distal end portion 14 of the surgical instrument 10 along the central axis thereof, such that the illumination axis of the lighting device angularly intersects the central axis of the surgical instrument 10, as best seen in FIG. 57.

Each engagement flange of the clamping mechanism is provided with an elastomeric plate 128' and 128" on interior surface thereof for engaging the distal end portion of the surgical instrument, and the spaced apart engagement flanges 124 and 126 are biased into the closed position of FIG. 66 by a biasing spring 132. The clamping arms 124 and 126 are attached to the conical shaft portion 122 of the adapter assembly 70 by a central boss 136 and retaining ring 134. The elastomeric plates 128' and 128" advantageously increase the compatibility of the adapter assembly with various shaped devices.

Referring now to FIGS. 73-78, there is illustrated an adapter assembly 80 for attaching one or more battery powered lighting devices 20 to a table 70. The adapter assembly 80 includes a U-shaped mounting clamp 142 and pressure bolt 144 for releasably attaching the assembly 80 to a table 70. The adapter assembly 80 further includes a pair of independently adjustable flexible adapter arms 146, each having a conical shaft portion 148 for releasably retaining a respective lighting device 20.

The subject invention is also directed to a kit that includes a handheld surgical instrument 10, a battery powered lighting device 20, an adapter for attaching lighting device to the surgical instrument (e.g., adapter 30 or 70), and a packaging enclosure containing the surgical instrument 10, the lighting device 20 and the adapter (e.g., adapter 30 or 70). Preferably, the handheld surgical instrument 20 is an electrosurgical pencil.

While the subject disclosure has been shown and described with reference to preferred embodiments, those skilled in the art will readily appreciate that changes or modifications may be made thereto without departing from the spirit or scope of the subject disclosure.

What is claimed is:

1. An adapter assembly for attaching a lighting device to a handheld surgical instrument comprising:
    a) a conical sleeve having an interior bore configured to engage a distal end portion of the surgical instrument at a position along a central axis thereof; and
    b) a housing formed integral with and extending radially outwardly from the conical sleeve and having an interior chamber for supporting the lighting device, which includes an LED light source and a lens located at a distal end of the housing to define the illumination axis of the lighting device, wherein the illumination axis of the lighting device angularly intersects the central axis of the surgical instrument, and wherein the interior bore of the conical sleeve and the interior chamber of the housing are separated from one another by a shared interior wall.

2. An adapter assembly as recited in claim 1, wherein the conical sleeve is bifurcated so as to form flexible conical sections for engaging the distal end portion of the surgical instrument.

3. An adapter assembly as recited in claim 1, wherein the conical sleeve is adapted for axial rotation about the central axis of the surgical instrument.

4. An adapter assembly as recited in claim 3, wherein a resilient O-ring is positioned within the interior bore of the conical sleeve for sealing against the distal end portion of the surgical instrument to prevent unwanted axial rotation of the conical sleeve without the application of a rotational force.

5. An adapter assembly as recited in claim 1, wherein a switching mechanism is disposed within the housing and it communicates with the conical sleeve for activating the LED light source upon engagement of the distal end portion of the surgical instrument with the conical sleeve.

6. An adapter assembly for attaching a lighting device to a handheld surgical instrument comprising:
    a) a housing having an interior chamber for supporting the lighting device, which includes an LED light source and a lens located at a distal end of the housing to define the illumination axis of the lighting device; and
    b) a clamping mechanism depending from the housing and including a pair of spaced apart engagement flanges adapted for linear movement between an open position for receiving the distal end portion of the surgical instrument and a closed position for engaging the distal end portion of the surgical instrument at a position along a central axis thereof, such that the illumination axis of the lighting device angularly intersects the central axis of the surgical instrument, wherein the pair of spaced apart engagement flanges are parallel to one another in the open position and the closed position.

7. An adapter assembly as recited in claim 6, wherein each engagement flange of the clamping mechanism is provided with an elastomeric plate on interior surface thereof for engaging the distal end portion of the surgical instrument, and the spaced apart engagement flanges are spring biased into the closed position.

8. An adapter assembly as recited in claim 6, wherein a switching mechanism is disposed within the housing for activating the LED light source upon engagement of the distal end portion of the surgical instrument with the clamping mechanism.

* * * * *